(12) United States Patent
Baraldi

(10) Patent No.: US 6,448,253 B1
(45) Date of Patent: Sep. 10, 2002

(54) ADENOSINE $A_3$ RECEPTOR MODULATORS

(75) Inventor: Pier Giovanni Baraldi, Ferrara (IT)

(73) Assignee: King Pharmaceuticals Research and Development, Inc., Cary, NC (US)

( * ) Notice: Subject to any disclaimer, the term of this patent is extended or adjusted under 35 U.S.C. 154(b) by 0 days.

(21) Appl. No.: 09/154,435

(22) Filed: Sep. 16, 1998

(51) Int. Cl.$^7$ .................... A61K 31/505; C07D 487/12; A61P 9/00

(52) U.S. Cl. ........................ 514/267; 544/251

(58) Field of Search ................... 514/267; 544/251

(56) References Cited

U.S. PATENT DOCUMENTS

| | | | |
|---|---|---|---|
| 3,625,214 A | 12/1971 | Higuchi | 128/260 |
| 4,789,734 A | 12/1988 | Pierschbacker | 530/395 |
| 4,906,474 A | 3/1990 | Langer et al. | 424/428 |
| 4,925,673 A | 5/1990 | Steiner et al. | 424/455 |
| 5,688,774 A | 11/1997 | Jacobson et al. | 514/46 |

FOREIGN PATENT DOCUMENTS

| | | |
|---|---|---|
| WO | 95/01356 | 1/1995 |
| WO | 96/38728 | 12/1996 |
| WO | 97/05138 | 2/1997 |

OTHER PUBLICATIONS

Abbracchio, M. P., et al., "G Protein–Dependent Activation of Phospholipase C by Adenosine $A_3$ Receptor in Rat Brain," *Mol. Pharmacol.*, 48: 1038–1045, 1995.

Ali, H. et al., "Sustained Activation of Phospholipase D via Adenosine $A_3$ Receptors is Associated with Enhancement of Antigen–and $Ca^{2+}$–Ionophore–Induced Secretion in a Rat Mast Cell Line," *J. Pharmacol. Exp. Ther.*, 276(2): 837–845, 1996.

Baraldi, P. G., et al., "Current Developments of $A_{2A}$ Adenosine Receptor Antagonists," *Curr. Med. Chem.*, 2: 707–722, 1995.

Baraldi, P.G., et al., "Novel $N^6$–(Substituted–phenylcarbomoyl) adenosine–5'–uronamides as Potent Agonists for $A_3$ Adenosine Receptors," *J. Med. Chem.*, 39(3): 802–806, 1996.

Baraldi, P. G., et al., "Synthesis of New Pyrazolo[4,3-e]-1,2,4-Triazolo[1,5-c]Pyrimidine and 1,2,3-Triazolo[4,5-e]-1,2,4-Triazolo[1,5-c]Pyrimidine Displaying Potent and Selective Activity as $A_{2A}$ Adenosine Receptor Antagonists," *Bioorg. Med. Chem. Lett.*, 4(21): 2539–2544, 1994.

Baraldi, P. G., et al., "Synthesis and Biological Activity of a New Series of $N^6$–Arylcarbamoyl, 2-(Ar)alkynyl-$N^6$–arylcarbamoyl, and $N^6$–Carboxamido Derivatives of Adenosine–5'–N–ethyluronamide as $A_1$ and $A_3$ Adenosine Receptor Agonists," *J. Med. Chem.*, 41(17): 3174–3185, 1998.

Bradford, M. M., "A Rapid and Sensitive Method for the Quantitation of Microgram Quantities of Protein Utilizing the Principle of Protein–Dye Binding", *Anal. Biochem.*, 72:248–254, 1976.

Bruns, R. F., et al., "Adenosine receptors in brain membranes: Binding of $N^6$–cyclohexyl[$^3$H]adenosine and 1,3–diethyl–8–[$^3$H]phenylxanthine", *Proc. Natl. Acad. Sci. USA*, 77(9): 5547–5551, 1980.

Cheng, Y–Chi, et al., "Relationship Between the Inhibition Constant ($K_1$) and the Concentration of Inhibitor Which Causes 50 Per Cent Inhibition ($I_{50}$) of an Enzymatic Reaction", *Biochem. Pharmacol*, 22:3099–3108, 1973.

Fredholm, B. B., et al., "VI. Nomenclature and Classification of Purinoceptors," *Pharmacol. Rev.*, 46(2): 143–156, 1994.

Gregoriadis, G., "Liposomes", *Drug Carriers in Biology and Med.*, 14: 287–341, 1979.

Hannon, J. P., et al., "A role for mast cells in adenosine $A_3$ receptor–mediated hypotension in the rat," *Br. J. Pharmacol.*, 115: 945–952, 1995.

Hill, R. J., et al., "Cloning, Expression and Pharmacological Characterization of Rabbit $A_1$ and $A_3$ Receptors," *J. Pharmacol. Exp. Ther.*, 280(1): 122–128, 1997.

Jacobson, K. A., et al., "Development of Selective Purinoceptor Agonists and Antagonists", *Purinergic Approaches in Experimental Therapeutics*, 6: 101–128, 1997.

Jacobson, K. A., et al., "Recent Developments in Selective Agonists and Antagonists Acting at Purine and Pyrimidine Receptors," *Drug Dev. Res.*, 39: 289–300, 1996.

Jiang, J. –L., et al., "6–Phenyl–1,4–dihydropyridine Derivatives as Potent and Selective $A_3$ Adenosine Receptor Antagonists," *J. Med. Chem.*, 39: 4667–4675, 1996.

Jiang, J. –L., et al., "Structure–Activity Relationships of 4–(Phenylethynl)–6–phenyl–1,4–dihydropyridines as Highly Selective $A_3$ Adenosine Receptor Antagonists," *J. Med. Chem.*, 40:2596–2608, 1997.

Kagan, J., et al., "The Synthesis and Phtochemistry of 4–Amino–3–cyanopyrazole", *J. Heter. Chem.*, 16(6): 1113–1115, 1979.

Karton, Y., et al., "Synthesis and Biological Activities of Flavonoid Derivatives as $A_3$ Adenosine Receptor Antagonists," *J. Med. Chem.*, 39: 2293–2301, 1996.

(List continued on next page.)

*Primary Examiner*—Brenda Coleman
(74) *Attorney, Agent, or Firm*—Roberts Abokhair & Mardula, LLC

(57) ABSTRACT

The compounds of formula I wherein R, $R^1$, $R^2$ $R^3$ and A have the meanings given in the specification, are endowed with selective $A_3$ adenosine receptor agonist activity. These compounds can be used in a pharmaceutical composition to treat disorders caused by excessive activation of the $A_3$ receptor, or can be used in a diagnostic application to determine the relative binding of other compounds to the $A_3$ receptor.

19 Claims, 1 Drawing Sheet

OTHER PUBLICATIONS

Kim, Y. C., et al., "Derivatives of the Triazoloquinazoline Adenosine Antagonist (CGS15943) Are Selective for the Human $A_3$ Receptor Subtype," *J. Med. Chem.*, 39: 4142–4148, 1996.

Kim, Y. C., et al., "Derivatives of the Triazoloquinazoline Adenosine Antagonist (CGS15943) Having High Potency at the Human $A_{2B}$ and $A_3$ Receptor Subtypes," *J. Med. Chem.*, 41: 2835–2845, 1998.

Li, A. –H., et al., "Structure–Activity Relationships and Molecular Modeling of 3,5–Diacyl–2,4–dialkylpyridine Derivatives as Selective $A_3$ Adenosine Receptor Antagonists," *J. Med. Chem.*, 41: 3186–3201, 1998.

Linden, J., "Cloned adenosine $A_3$ receptors: pharmacological properties, species differences and receptor functions," *TIPS*, 15: 298–306, 1994.

Linden, J., et al., "Molecular Cloning and Functional Expression of a Sheep $A_3$ Adenosine Receptor With Widespread Tissue Distribution," *Mol. Pharmacol.*, 44: 524–532, 1993.

Lohse, M. J., et al., "8–Cyclopentyl 1–3diprophlxanthine (DPCPX)–a selective high affinity antagonist radioligand for $A_1$ adenosine receptors," *Naunyn–Schmiedeberg's Arch. Pharmacol.*, 336: 204–210, 1987.

Lubitz, D. K. J. E. Von, et al., "The effects of adenosine $A_3$ receptor stimulation on seizures in mice," *Eur. J. Pharmacol.*, 275: 23–29, 1995.

Lubitz, D. K. J. Von, et al., "Adenosine $A_3$ receptor stimulation and cerebral ischemia," *Eur. J. Pharmacol.*, 263: 59–67, 1994.

MacKenzie, W. M., et al., "Adenosine Inhibits the Adhesion of Anti–CD3–activated Killer Lymphocytes to Adenocarcinoma Cells Through an $A_3$ Receptor," *Cancer Res.*54: 3521–3526, 1994.

Meade, C. J. et al., "In Vivo Role of the Adenosine $A_3$ Receptor–N6–2–(4–aminophenyl) Ethyladenosine Induces Broncospasm in BDE Rats by a Neurally Mediated Mechanism Involving Cells Resembling Mast Cells," *J. Pharm. Exp. Ther.*, 279(3): 1148–1156, 1996.

Meyerhof, W., et al., "Molecular cloning of a novel putative G–protein coupled receptor expressed during rat spermiogenesis," *FEBS Lett.*, 284(2): 155–160, 1991.

Moro, S., et al., "Flavonoid Derivatives as Adenosine Receptor Antagonists: a Comparison of the Hypothetical Receptor Binding Site Based on a Comparative Molecular Field Analysis Model," *J. Med. Chem.*, 41(1): 46–52, 1998.

Munson, P. J., et al., "LIGAND: A Versatile Computerized Approach for Characterization of Ligand–Binding Systems", *Ana. Biochem.*, 107: 220–239, 1980.

Olah, M. E., et al., "ADENOSINE RECEPTOR SUBTYPES: Characterization and Therapeutic Regulation," *AnnU. Rev. Pharmacol. Toxicol.*, 35: 581–606, 1995.

Ramkumar, V., et al., "The $A_3$ Adenosine Receptors is the Unique Adenosine Receptor Which Facilitates Release of Allergic Mediators in Mast Cells", *J. Biol. Chem.*, 268: 16887–16890, 1993.

Sajjadi, F. G., et al., "cDNA cloning and sequence analysis of the human $A_3$ adenosine receptor," *Biochim. Biophys. Acta*, 1179: 105–107, 1993.

Salvatore, C. A., et al., "Molecular cloning and characterization of the human $A_3$ adenosine receptor," *Proc. Natl. Acad. Sci. U.S.A.*, 90: 10365–10369, 1993.

Schaick, E. A. Van, et al., "Haemodynamic effects and histamine release elicited by the selective adenosine $A_3$ receptor agonists 2–Cl–IB–MECA in conscious rats", *Eur. J. Pharmacol.*, 308: 311–314, 1996.

van Muijlwijk–Koezen, J. E., et al., "A Novel Class of Adenosine $A_3$ Receptor Ligands. 1.3–(2–Pyridinil)isoquinoline Derivatives", *J. Med. Chem.*, 41(21): 3987–3993, 1998.

van Muijlwijk–Koezen, J. E., et al, "A Novel Class of Adenosine $A_3$ Receptor Ligands. 2. Structure Affinity Profile of a Series of Isoquinoline and Quinazoline Compounds", *J. Med. Chem.*, 41(21): 3994–4000, 1998.

van Rhee, A. M., et al., "Interaction of 1,4–Dihydropyridine and Pyridine Derivatives with Adenosine Receptors: Selectivity for $A_3$ Receptors," *J. Med. Chem.*, 39:2980–2989, 1996.

Zhao, Z., et al., "Chromosomal Mapping of the Mouse $A_3$ Adenosine Receptor Gene, Adora3," *Genomics*, 30: 118–119, 1995.

Baraldi, P.G., et al., "1,2,3–Triazolo[5,4–e]1,2,4–Triazolo[1, 5–c]Pyrimidine Derivatives: A New Class of $A_{2A}$ Adenosine Receptor Antagonists," *IL FARMACO*, vol. 51, No. 4 pp. 297–300 (1996).

Baraldi, P.G., et al., "1H–Pyrazolo[4,3–d] pyrimidine–7(6H)–one and 5H–Pyrazolo[4,3–d]1,2, 3–triazin–4(3H)–one Derivatives," Arzneimittel Forschung Drug Research, vol. 46, pp. 365–368 (1996).

Baraldi, P.G., et al., "Design, Synthesis and Biological Evaluation of a Second Generation of Pyrazolo[4,3–e]–1,2, 4–triazolo[1,5–c]pyrimidines as Potent and Selective $A_{2A}$ Adenosine Receptor Antagonists," *J. Med. Chem.*, vol. 41, No. 12, pp. 2126–2133 (1998).

Baraldi, P.G., et al., "Pyrazolo[4,3–e]–1,2,4–triazolo[1,5–c] pyrimidine Derivatives: Potent and Selective $A_{2A}$ Adenosine Antagonists," *J. Med. Chem.*, vol. 39, No. 5, pp. 1164–1171 (1996).

Baraldi, P.G., et al. "Synthesis of 1H–Pyrazolo[4,3–d] pyrimidine–7(6H)–ones and Pyrazolo–5–carboxamides and Interaction with Benzodiazepine and Adenosine $A_1$ Receptors in Rat Cerebral Cortex," Arzneim.–Forsch. Drug Res., vol. 38, No. 11, pp. 1262–1265 (1988).

Baraldi, P.G., et al., "Synthesis of 3–Substituted–7–alkoxy–5H–pyrazolo[4,3–d]–1,2, 3–triazin–4–(3H)–ones," Journal of Synthetic Organic Chemistry, vol. 12, pp. 1437–1440 (1994).

Baraldi, P.G., et al., "Synthesis of the Tritium Labeled SCH 58261, a New Non–Xanthine $A_{2A}$ Adenosine Receptor Antagonist," Journal of Labelled Compounds and Radiopharm., vol. XXXVIII, No. 8, pp. 725–732 (1996).

Cheng, C.C., et al., "Potential Purine Antagonists, VI. Synthesis of 1–Alkyl–and 1–Aryl–4–substituted Pyrazolo[3, 4–d]pyrimidines$^{1,2}$," J. Org. Chem., vol. 21, pp. 1240–1256 (1956).

Crooks, P.A., et al., "Synthesis of 5–Benzoyl–5–phenyl–and 5–Phenylhydroxymethyl–5–phenylhydantoins as Potential Anticonvulsants," J. Heterocyclic Chem., vol. 26, No. 4 pp. 1113–1117 (1989).

Jacobson, "Adenosine $A_3$ receptors: novel ligands and paradoxical effects," TIPS, pp. 184–191 (May 1998).

Mathot et al., "Deoxyribose analogues of $N^6$–cyclopentyladenosine (CPA): partial agonists at the adenosine $A_1$ receptor in vivo," Brit. J. Pharmacol., vol. 116, pp. 1957–1964 (1995).

Shryock, John C., "FSPTP: The First Irreversible Anatagonist of the A2a–Adenosine Receptor," Abstracts From the 70th Scientific Sessions, vol. 96, No. 8, pp. 287 (1997).

Shultz, J.F., et al., Journal of the American Chemical Society, vol. 78, pp. 284 (1956).

Takagi, K., et al., "Sur la Formation d'un Dérivé Pyrazolique Original à partir d'Hydrazine et d'Ethoxyméethylène Malononitrile," Chem. Pharm. Bull., vol. 18, pp. 2353–2356 (1970).

van Calenbergh, "$N_6$–Cyclopentyl–3'–substituted–xylofuranosyladenosines: A New Class of Non–Xanthine Adenosine $A_1$ Receptor Antagonists," J. Med. Chem., vol. 40, pp. 3765–3772 (1997).

van der Wenden et al., "Ribose–Modified Adenosine Analogues as Potential Partial Agonists for the Adenosine Receptor," J. Med. Chem., vol. 38, pp. 4000–4006 (1995).

Zocchi, Cristina et al., "Binding of the radioligand [$^3$H]–SCH 58261, a new non–xanthine $A_{2A}$ adenosine receptor antagonist, to rat striatal membranes," British Journal of Pharmacology, vol. 117, No. 7, pp. 1381–1386 (1996).

Zocchi, C., et al., "SCH 58261, A New Potent and Selective Adenosine $A_{2a}$ Receptor Antagonist," British Journal of Pharmacology, vol. 114, pp. 229–300 (1995).

Zocchi, Cristina et al., "The Non–Xanthine Heterocylic Compound SCH 58261 is a New Potent and Selective $A_{2a}$ Adenosine Receptor Antagonist," The Journal of Pharmacology and Experimental Therapeutics, vol. 276, No. 2, pp. 398–276 (1996).

SATURATION OF [$^{125}$I]-AB-MECA BINDING TO HUMAN A$_3$ RECEPTORS EXPRESSED IN HEK 293 CELLS

ADENOSINE A₃ RECEPTOR MODULATORS

FIELD OF THE INVENTION

The present invention relates to certain pyrazolo-triazolo-pyrimidine, triazolo-triazolo-pyrimidine and imidazolo-triazolo-pyrimidine derivatives and their use in the practice of medicine as modulators of adenosine $A_3$ receptors.

BACKGROUND OF THE INVENTION

Three major classes of adenosine receptors, classified as $A_1$, $A_2$, and $A_3$, have been characterized pharmacologically. $A_1$ receptors are coupled to the inhibition of adenylate cyclase through $G_i$ proteins and have also been shown to couple to other second messenger systems, including inhibition or stimulation of phosphoinositol turnover and activation of ion channels. $A_{2A}$ receptors are further divided into two subtypes, $A_{2A}$ and $A_{2B}$, at which adenosine agonists activate adenylate cyclase with high and low affinity, respectively. The $A_3$ receptor sequence was first identified in a rat testes cDNA library, and this sequence, later cloned by homology to other G-protein coupled receptors from a rat brain cDNA library, was shown to correspond to a novel, functional adenosine receptor.

The discovery of the $A_3$ receptor has opened new therapeutic vistas in the purine field. In particular, the $A_3$ receptor mediates processes of inflammation, hypotension, and mast cell degranulation. This receptor apparently also has a role in the central nervous system. The $A_3$ selective agonist IB-MECA induces behavioral depression and upon chronic administration protects against cerebral ischemia. $A_3$ selective agonists at high concentrations were also found to induce apoptosis in HL-60 human leukemia cells. These and other findings have made the $A_3$ receptor a promising therapeutic target. Selective antagonists for the $A_3$ receptor are sought as potential anti inflammatory or possibly anti-ischemic agents in the brain. Recently, $A_3$ antagonists have been under development as antiasthmatic, antidepressant, antiarrhythmic, renal protective, antiparkinson and cognitive enhancing drugs.

It is therefore an object of the present invention to provide compounds and methods of preparation and use thereof, which are agonists, partial agonists, and/or antagonists of the adenosine $A_3$ receptor.

SUMMARY OF THE INVENTION

Compounds useful as potent, yet selective modulators of the adenosine $A_3$ receptor, with activity as antagonists of this receptor, and methods of preparation and use thereof, are disclosed.

The compounds have the following general formula:

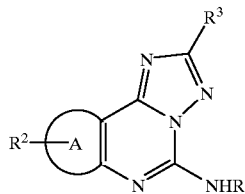

wherein:

A is imidazole, pyrazole, or triazole;

R is $-C(X)R^1$, $-C(X)-N(R^1)_2$, $-C(X)OR^1$, $-C(X)SR^1$, $-SO_nR^1$, $-SO_nOR^1$, $-SO_nSR^1$ or $SO_n-N(R^1)_2$;

$R^1$ is hydrogen, alkyl, substituted alkyl, alkenyl, substituted alkenyl, alkynyl, substituted alkynyl, aryl, heteroaryl, heterocyclic, lower alkenyl, lower alkanoyl, or, if linked to a nitrogen atom, then taken together with the nitrogen atom, forms an azetidine ring or a 5–6 membered heterocyclic ring containing one or more heteroatoms such as N, O, S;

$R^2$ is hydrogen, alkyl, substituted alkyl, aralkyl, substituted aralkyl, heteroaryl, substituted heteroaryl or aryl;

$R^3$ is furan, pyrrole, thiophene, benzofuran, benzopyrrole, benzothiophene, optionally substituted with one or more substituents as described herein for substituted heteroaryl rings;

X is O, S, or $NR^1$;

n is 1 or 2; and and pharmaceutically acceptable salts thereof.

Preferably, $R^1$ is hydrogen; C1 to C8 alkyl; C3 to C7 alkenyl, C3 to C7 alkynyl; C3 to C7 cycloalkyl; C1 to C5 alkyl substituted with one or more halogen atoms, hydroxy groups, C1 to C4 alkoxy, C3 to C7 cycloalkyl or groups of formula $-NR^1_2$, $-CONR^1_2$; aryl, substituted aryl wherein the substitution is selected from the group consisting of C1 to C4 alkoxy, C1 to C4 alkyl, nitro, amino, cyano, C1 to C4 haloalkyl, C1 to C4 haloalkoxy, carboxy, carboxyamido; C7 to C10 aralkyl in which the aryl moiety can be substituted with one or more of the substituents indicated above for the aryl group; a group of formula $-(CH_2)m$-Het, wherein Het is a 5–6 membered aromatic or non aromatic heterocyclic ring containing one or more heteroatoms selected from the group consisting of N, O, and S and m is an integer from 1 to 5;

Preferred C1 to C8 alkyl groups are methyl, butyl and isopentyl. Examples of C3 to C7 cycloalkyl groups include cyclopropyl, cyclopentyl, and cyclohexyl. Examples of C1 to C5 alkyl groups substituted with C3 to C7 cycloalkyl groups include cyclohexylmethyl, cyclopentylmethyl, and 2-cyclopentylethyl. Examples of substituted C1 to C5 alkyl groups include 2-hydroxyethyl, 2-methoxyethyl, trifluoromethyl, 2-fluoroethyl, 2-chloroethyl, 3-aminopropyl, 2-(4methyl-1-piperazine)ethyl, 2-(4-morpholinyl)ethyl, 2-aminocarbonylethyl, 2-dimethylaminoethyl, 3-dimethylaminopropyl. Aryl is preferably phenyl, optionally substituted with Cl, F, methoxy, nitro, cyano, methyl, trifluoromethyl, difluoromethoxy groups. Examples of 5 to 6 membered ring heterocyclic groups containing N, O and/or S include piperazinyl, morpholinyl, thiazolyl, pyrazolyl, pyridyl, furyl, thienyl, pyrrolyl, triazolyl, tetrazolyl. Examples of C7 to C10 aralkyl groups comprise benzyl or phenethyl optionally substituted by one or more substituents selected from Cl, F, methoxy, nitro, cyano, methyl, trifluoromethyl, and difluoromethoxy. Preferably, R is hydrogen, C1 to C8 alkyl, aryl or C7 to C10 aralkyl, optionally substituted, preferably with halogen atoms.

Particularly preferred compounds are those in which R is a phenethyl group in which the phenyl ring is substituted with one or more substituents selected from the group consisting of chlorine, fluorine atoms, methoxy, nitro, cyano, methyl, trifluoromethyl, and difluoromethoxy groups.

The possible meanings of A can be represented by the following structural formulae:

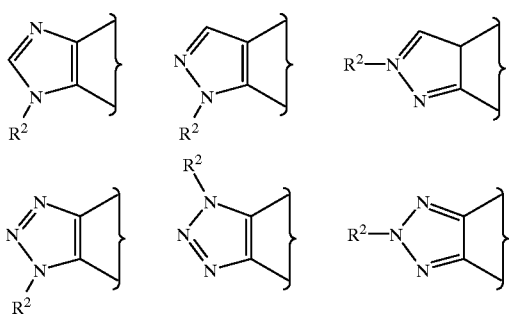

The compounds can be used in a method for modulating adenosine $A_3$ receptors in a mammal, including a human. The methods involve administering an effective amount of a compound of formula I sufficient to modulate adenosine $A_3$ receptors in the mammal. Uses for the compounds include:

treating hypertension;

treating inflammatory disorders such as rheumatoid arthritis and psoriasis;

treating allergic disorders such as hay fever and allergic rhinitis;

mast cell degranulation;

antitumor agents;

treating cardiac hypoxia; and protection against cerebral ischemia;

diagnostic uses, for example, to determine the presence of one or more of the above described medical conditions, or in a screening assay to determine the effectiveness of other compounds for binding to the $A_3$ Ado receptor (i.e., through competitive inhibition as determined by various binding assays), as described in Jacobson and Van Rhee, Purinergic approaches to experimental therapy, Jacobson and Jarvis, ed., Wiley, N.Y., 1997, pp. 101–128; Mathot et al., *Brit. J. Pharmacol.*, 116:1957–1964 (1995); van der Wenden et al., *J. Med. Chem.*, 38:4000–4006 (1995); and van Calenbergh, *J. Med. Chem.*, 40:3765–3772 (1997), the contents of which are hereby incorporated by reference.

The compounds can also be used in a method for fully or partially inhibiting adenylate cyclase ($A_3$) in a mammal, including a human. The methods involve administering an effective amount of a compound of formula I sufficient to fully or partially inhibiting adenylate cyclase in the mammal.

The compounds can be used in a pharmaceutical formulation that includes a compound of formula I and one or more excipients. Various chemical intermediates can be used to prepare the compounds.

DETAILED DESCRIPTION OF THE INVENTION

Figure 1:
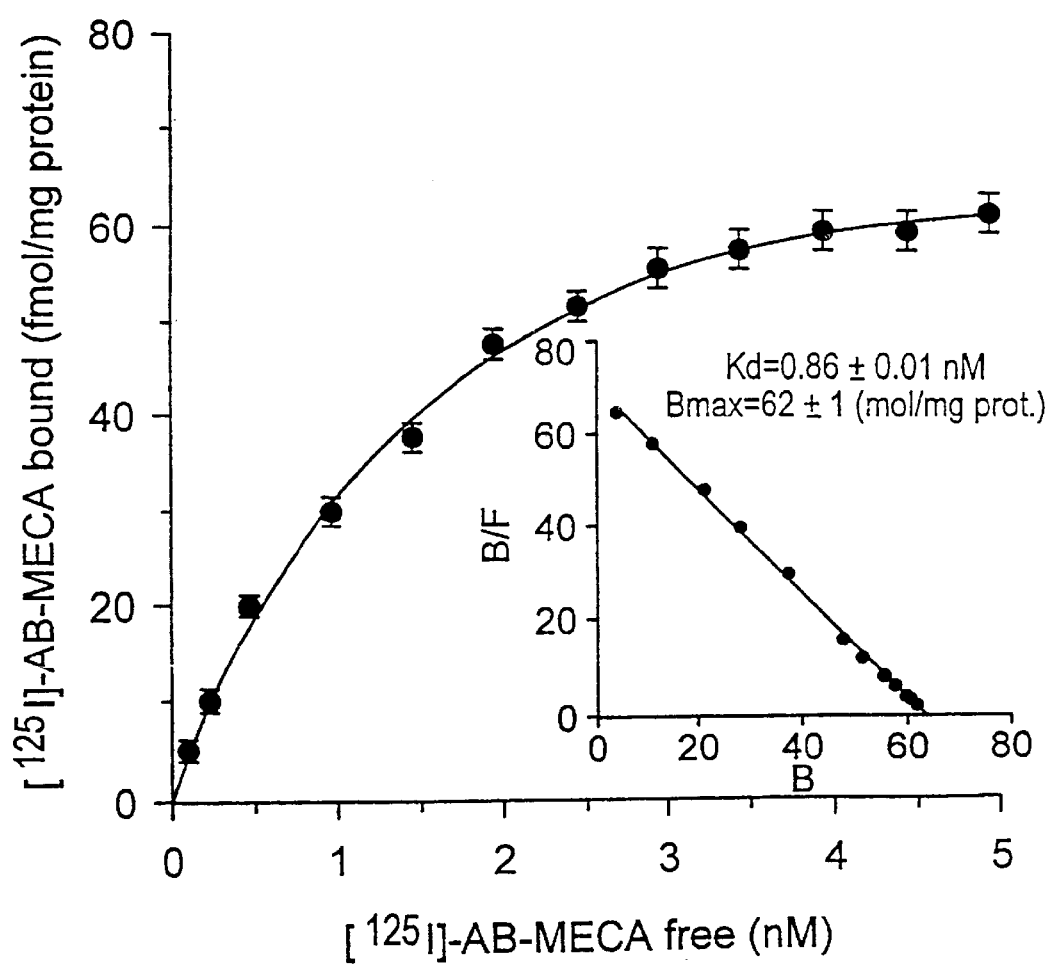
FIG. 1 is a graph showing the saturation of $[^{125}I]$AB-MECA binding (fmol/mg protein) to human $A_3$ receptors expressed in HEK 293 cells versus the molar concentration of $[^{125}I]$AB-MECA.

The present application discloses compounds useful as potent, yet selective modulators of adenosine receptors, with activity as $A_3$ agonists, and in some cases, $A_3$ antagonists, and methods of preparation and use thereof.

The compounds can be used in a method for modulating adenosine $A_3$ receptors in a mammal, including a human. The methods involve administering an effective amount of a compound of formula I sufficient to moderate adenosine $A_3$ receptors to the mammal.

The compounds can be used in a pharmaceutical formulation that includes a compound of formula I and one or more excipients. Various chemical intermediates can be used to prepare the compounds.

Definitions

As used herein, a compound is an agonist of an adenosine $A_1$ receptor if it is able to fully inhibit adenylate cyclase ($A_3$) and is able to displace $[^{125}I]$-AB-MECA in a competitive binding assay.

As used herein, a compound is a partial agonist of an adenosine $A_3$ receptor if it is able to partially inhibit adenylate cyclase ($A_3$) and is able to displace $[^{125}I]$-AB-MECA in a competitive binding assay.

As used herein, a compound is an antagonist of an adenosine $A_3$ receptor if it is able to prevent the inhibition due to an agonist and is able to displace $[^{125}I]$-AB-MECA in a competitive binding assay.

As used herein, a compound is selective for the $A_3$ receptor if the ratio of $A_1/A_3$ and $A_2/A_3$ activity is greater than about 50, preferably between 50 and 100, and more preferably, greater than about 100.

As used herein, the term "alkyl" refers to monovalent straight, branched or cyclic alkyl groups preferably having from 1 to 20 carbon atoms, more preferably 1 to 10 carbon atoms ("lower alkyl") and most preferably 1 to 6 carbon atoms. This term is exemplified by groups such as methyl, ethyl, n-propyl, iso-propyl, -butyl, iso-butyl, n-hexyl, and the like. The terms "alkylene" and "lower alkylene" refer to divalent radicals of the corresponding alkane. Further, as used herein, other moieties having names derived from alkanes, such as alkoxyl, alkanoyl, alkenyl, cycloalkenyl, etc when modified by "lower," have carbon chains of ten or less carbon atoms. In those cases where the minimum number of carbons are greater than one, e.g., alkenyl (minimum of two carbons) and cycloalkyl, (minimum of three carbons), it is to be understood that "lower" means at least the minimum number of carbons.

As used herein, the term "substituted alkyl" refers to an alkyl group, preferably of from 1 to 10 carbon atoms ("substituted lower alkyl"), having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino aminoacyl, aminoacyloxy, oxyacylamino, cyano, halogen, hydroxyl, keto, thioketo, carboxyl, carboxylalkyl, thiol, thioalkoxy, substituted thioalkoxy, aryl, aryloxy, heteroaryl, heteroaryloxy, heterocyclic, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, aryl, heteroaryl and heterocyclic. As used herein, other moieties having the prefix "substituted" are intended to include one or more of the substituents listed above.

As used herein, the term "alkoxy" refers to the group "alkyl-O—", where alkyl is as defined above. Preferred alkoxy groups include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

As used herein, the term "alkenyl" refers to alkenyl groups preferably having from 2 to 10 carbon atoms and more preferably 2 to 6 carbon atoms and having at least 1 and preferably from 1–2 sites of alkenyl unsaturation. Preferred alkenyl groups include ethenyl (—CH=CH$_2$), n-propenyl (—CH$_2$CH=CH$_2$), iso-propenyl (—C(CH$_3$)=CH$_2$), and the like.

As used herein, the term "alkynyl" refers to alkynyl groups preferably having from 2 to 10 carbon atoms and more preferably 2 to 6 carbon atoms and having at least 1 and preferably from 1–2 sites of alkynyl unsaturation.

As used herein, the term "acyl" refers to the groups alkyl-C(O)—, substituted alkyl-C(O)—, cycloalkyl-C(O)—, substituted cycloalkyl-C(O)—, aryl-C(O)—, heteroaryl-C(O)— and heterocyclic-C(O)— where alkyl, substituted alkyl, cycloalkyl, substituted cycloalkyl, aryl, heteroaryl and heterocyclic are as defined herein.

As used herein, the term "acylamino" refers to the group —C(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

As used herein, the term "aryl" refers to an unsaturated aromatic carbocyclic group of from 6 to 14 carbon atoms having a single ring (e.g., phenyl) or multiple condensed (fused) rings (e.g., naphthyl or anthryl). Preferred aryls include phenyl, naphthyl and the like. Unless otherwise constrained by the definition for the aryl substituent, such aryl groups can optionally be substituted with from 1 to 5 substituents and preferably 1 to 3 substituents selected from the group consisting of hydroxy, acyl, alkyl, alkoxy, alkenyl, alkynyl, substituted alkyl, substituted alkoxy, substituted alkenyl, substituted alkynyl, amino, substituted amino, aminoacyl, acyloxy, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, trihalomethyl. Preferred substituents include alkyl, alkoxy, halo, cyano, nitro, trihalomethyl, and thioalkoxy.

As used herein, the term "cycloalkyl" refers to cyclic alkyl groups of from 3 to 12 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantyl, and the like.

As used herein, the terms "halo" or "halogen" refer to fluoro, chloro, bromo and iodo and preferably is either fluoro or chloro.

As used herein, the term "heteroaryl" refers to an aromatic carbocyclic group of from 1 to 15 carbon atoms and 1 to 4 heteroatoms selected from the group consisting of oxygen, nitrogen and sulfur within at least one ring (if there is more than one ring).

Unless otherwise constrained by the definition for the heteroaryl substituent, such heteroaryl groups can be optionally substituted with from 1 to 5 substituents and preferably 1 to 3 substituents selected from the group consisting of hydroxy, acyl, alkyl, alkoxy, alkenyl, alkynyl, substituted alkyl, substituted alkoxy, substituted alkenyl, substituted alkynyl, amino, substituted amino, aminoacyl, acyloxy, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and trihalomethyl. Preferred substituents include alkyl, alkoxy, halo, cyano, nitro, trihalomethyl, and thioalkoxy. Such heteroaryl groups can have a single ring (e.g., pyridyl or furyl) or multiple condensed rings (e.g., indolizinyl or benzothienyl).

"Heterocycle" or "heterocyclic" refers to a monovalent saturated or unsaturated group having a single ring or multiple condensed rings, from 1 to 15 carbon atoms and from 1 to 4 hetero atoms selected from the group consisting of nitrogen, sulfur and oxygen within the ring.

Unless otherwise constrained by the definition for the heterocyclic substituent, such heterocyclic groups can be optionally substituted with 1 to 5 substituents selected from the group consisting of alkyl, substituted alkyl, alkoxy, substituted alkoxy, aryl, aryloxy, halo, nitro, heteroaryl, thiol, thioalkoxy, substituted thioalkoxy, thioaryloxy, trihalomethyl, and the like. Such heterocyclic groups can have a single ring or multiple condensed rings.

As to any of the above groups that contain 1 or more substituents, it is understood, of course, that such groups do not contain any substitution or substitution patterns which are sterically impractical and/or synthetically non-feasible.

As used herein, "carboxylic acid derivatives" and "sulfonic acid derivatives" refer to —C(X)R$^1$, —C(X)—N(R$^1$)$_2$, —C(X)OR$^1$, —C(X)SR$^1$, —SO$_n$R$^1$, —SO$_n$OR$^1$, —SO$_n$SR$^1$ or —SO$_n$—N(R$^1$)$_2$; where X is O, S or NR$^1$, where R$^1$ is hydrogen, alkyl, substituted alkyl or aryl, and activated derivatives thereof, such as anhydrides, esters, and halides such as chlorides, bromides and iodides, which can be used to couple the carboxylic acid and sulfonic acid derivatives to the 5'-amine using standard coupling chemistry.

"Pharmaceutically acceptable salts" refers to pharmaceutically acceptable salts of a compound of Formulas IA, IB, or IC, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like can be used as the pharmaceutically acceptable salt.

The term "protecting group" or "blocking group" refers to any group which when bound to one or more hydroxyl, amino or carboxyl groups of the compounds (including intermediates thereof such as the aminolactams, aminolactones, etc.) prevents reactions from occurring at these groups and which protecting group can be removed by conventional chemical or enzymatic steps to reestablish the hydroxyl, amino or carboxyl group. Preferred removable amino blocking groups include conventional substituents such as t-butyoxycarbonyl (t-BOC), benzyloxycarbonyl (CBZ), and the like which can be removed by conventional conditions compatible with the nature of the product.

The following abbreviations are used herein: Abbreviations: [$^{125}$I]AB-MECA, [$^{125}$I]N$^6$-(4-amino-3-iodobenzyl)adenosine-5-N-methyluronamide;(R)-PIA, (R)-N$^6$-(phenylisopropyl)adenosine; DMSO, dimethysulfoxide; I-AB-MECA, N$^6$-(4-amino-3-iodobenzyl)adenosine-5-N- methyluronamide; IB-MECA, $N^6$-(3-iodobenzyl)adenosine-5-N-methyluronamide; Ki, equilibrium inhibition constant; NECA, 5-N-ethylcarboxamido adenosine; THF, tetrahydrofuran; Tris, tris(hydroxymethyl)aminomethane.

Compound Preparation

Those skilled in the art of organic chemistry will appreciate that reactive and fragile functional groups often must be protected prior to a particular reaction, or sequence of reactions, and then restored to their original forms after the last reaction is completed. Usually groups are protected by converting them to a relatively stable derivative. For example, a hydroxyl group may be converted to an ether group and an amine group converted to an amide or carbamate. Methods of protecting and de-protecting, also known as "blocking" and "de-blocking," are well known and widely practiced in the art, e.g., see T. Green, *Protective Groups in Organic Synthesis*, John Wiley, New York (1981) or *Protective Groups in Organic Chemistry*, Ed. J. F. W. McOmie, Plenum Press, London (1973).

The compounds are preferably prepared by reacting a compound of Formula II below with a suitable carboxylic acid or sulfonic acid derivative using known chemistry.

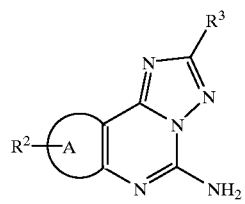

II

Compounds of Formula II can be prepared using the following Schemes I and II, illustrated where $R^3$ is furan.

Scheme I

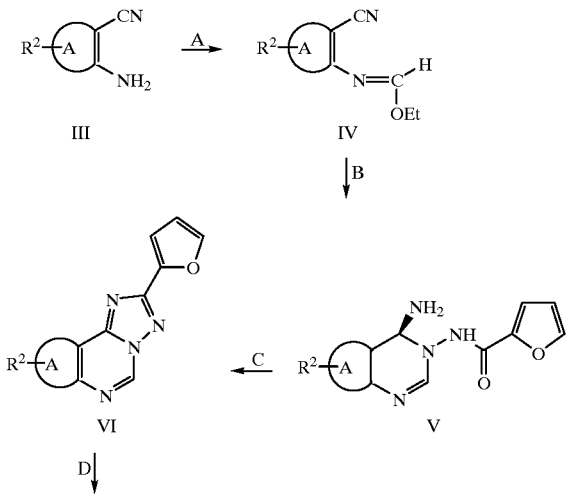

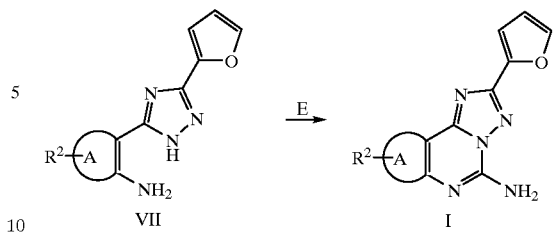

Reagents: A) triethyl orthoformate; B) 2-furoic acid hydrazide, 2-methoxyethanol; C) PhOPh, 260° C.; D) 10% HCl, under reflux; E) cyanamide, pTsOH, N-methylpyrrolidone Scheme II

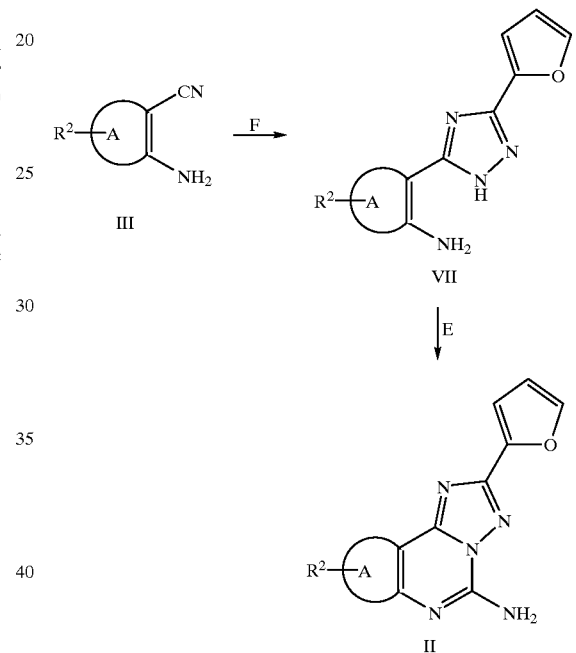

Reagents: F) furoic acid hydrazide, diphenyl ether; E) cyanamide, pTsOH, N-methylpyrrolidone.

The compounds of formula II can be prepared through either an indirect route described in Scheme I or a direct route described in Scheme II. Suitable starting materials for both schemes are the heterocyclic ortho-amino nitriles of formula III, generally prepared according to synthetic procedures known in literature and reported in the book by E. C. Taylor and A. McKillop (vol. 7 of the series Advances in Organic Chemistry, Ed. Interscience, 1970).

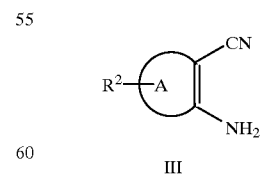

III

Ortho-amino nitrites III are transformed into the corresponding imidates of formula IV by reaction with an ethyl orthofornate excess at the reflux temperature for 8 to 10 h. The reaction, after evaporation of the ethyl orthoformate, leads to the substantially pure corresponding imidates IV in a high yield as evidenced by the IR and ¹H NMR analysis on the crude reaction products.

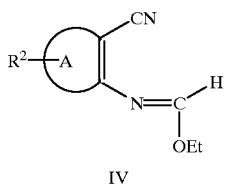

IV

The imidates of formula IV are then subjected to a sequence of two reactions allowing to obtain the tricyclic structures of formula VI in a high yield.

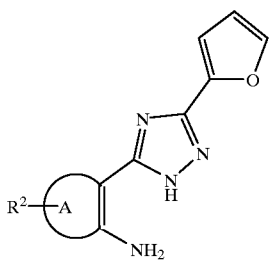

VI

The reaction sequence includes: a) reaction with 2-furoic acid hydrazide in a 2-methoxyethanol solution at the reflux temperature for 8–10 h, to obtain the intermediates compounds of formula V; b) thermal cyclization of the latter to corresponding compounds of formula VI, by heating in diphenyl ether at the temperature of 260° C. for 0.5 to 1 h.

The tricyclic compounds VI are then hydrolyzed with HCl at reflux for 1 to 3 h to give triazoles VII, which are finally cyclized to desired compounds II with cyanamide in N-methyl pyrrolidone at reflux and in the presence of para-toluenesulfonic acid (Scheme I).

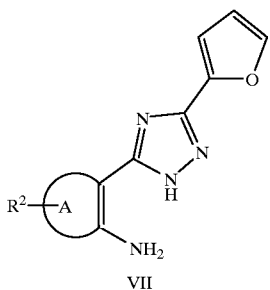

VII

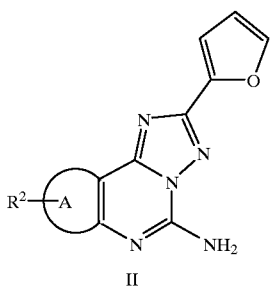

II

In some cases, triazoles VII can be obtained directly heating in diphenyl ether ortho-amino nitrile III with 2-furoic acid hydrazide. Triazoles VII are then cyclized as described above in Scheme II. In the following schemes III, IV and V, the synthesis of the compounds of formula II in which A is a triazole ring are reported in more detail.

Scheme III

Synthesis of 5-amino-7-substituted-2(2-furyl)-1,2,3-triazolo[5,4-e]1,2,4-triazolo[1,5-c]pyrimidine Derivatives

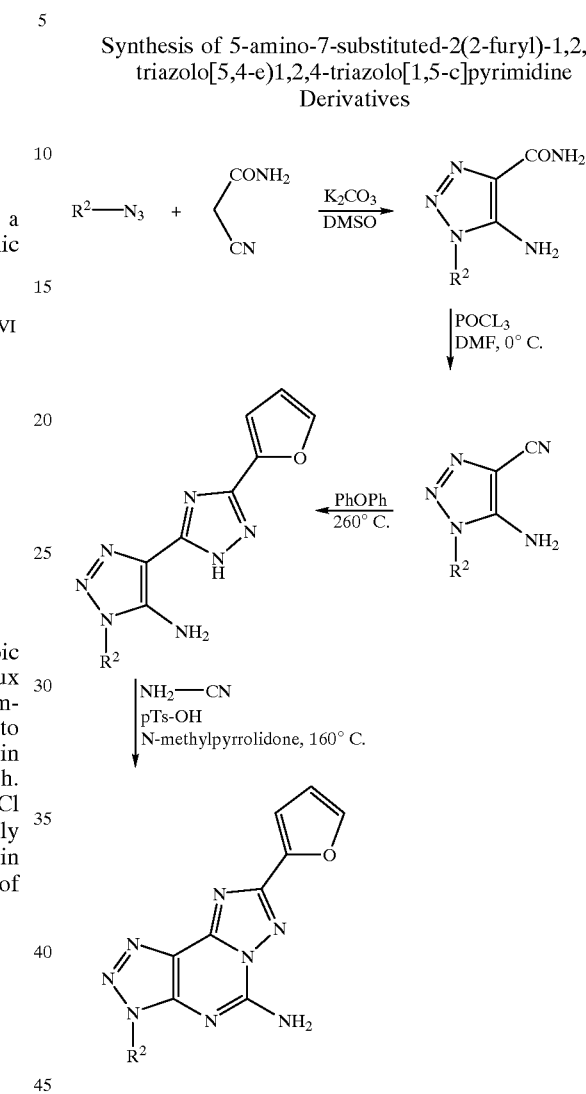

Scheme IV

Synthesis of 5-amino-8-substituted-2(2-furyl)-1,2,3-triazolo[5,4-e]1,2,4-triazolo[1,5-c]pyrimidine Derivatives

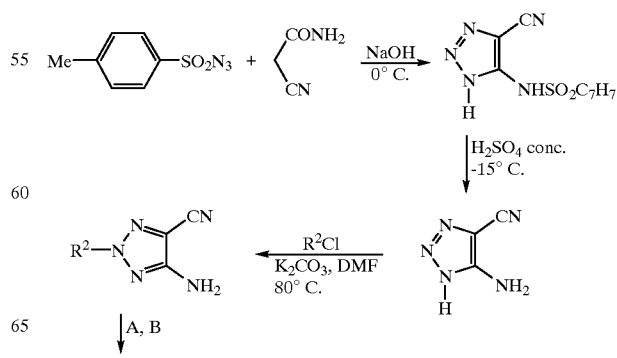

-continued

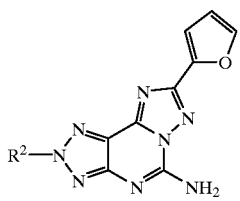

Reagents: A) furoic acid hydrazide, PhOph, 260° C.,
B) NH$_2$CN, pTsOH, N-methylpyrrolidone.

Scheme V

Synthesis of 5-amino-9-substituted-2(2-furyl)-1,2,3-triazolo[5,4-e]1,2,4-triazolo[1,5-c]pyrimidine Derivatives

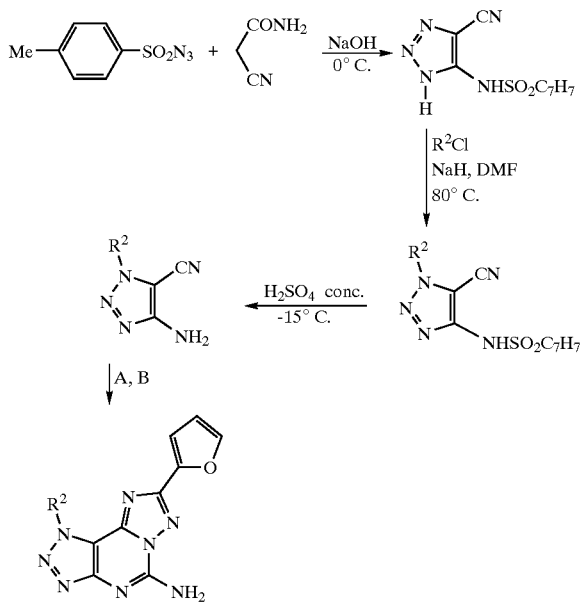

Reagents: A) furoic acid hydrazide, PhOph, 260° C.,
B) NH$_2$CN, pTsOH, N-methylpyrrolidone.

Finally, the 5-amine-containing compounds II are reacted with carboxylic acids, sulfonic acids, activated carboxylic acids, activated sulfonic acids, thiocarboxylic acids, activated thiocarboxylic acids, and the like, to form the desired compounds. Activated carboxylic acids include acid halides, esters, anhydrides and other derivatives known to react with amines to form amides. Activated sulfonic acids include sulfonyl halides such as sulfonyl chlorides.

It is not necessary in all cases to use activated carboxylic acid and sulfonic acid derivatives. The acids themselves can be coupled to the amines using standard coupling chemistry, for example, using dicyclohexyl diimide (DCI) and other routinely used coupling agents. Suitable coupling conditions for forming amide linkages are well known to those of skill in the art of peptide synthesis.

Generally, the chemistry above can be used to prepare 8-(Ar)alkyl-2-(2-furyl)-pyrazolo[4,3-e]-1,2,4-triazolo[1,5c] pyrimidines when 3-cyano-2-aminopyrazoles are used as starting materials. The 3-cyano-2-aminopyrazoles can be reacted with an alkyl halide (RX) in a polar aprotic solvent such as dimethyl formamide (DMF) to provide an R group on one of the ring nitrogens. The resulting compound can be refluxed with triethyl orthoformate to provide an imine ethyl ester, which can be reacted with furoic hydrazide, preferably using a Dean-Stark trap for the azeotropic elimination of water produced in the reaction, to provide 8-(Ar)alkyl-2-(2-furyl)-pyrazolo[4,3-e]-1,2,4-triazolo[1,5c]pyrimidines. The products can be purified by chromatography, for example, in (EtOAc/hexane 1:1), for use in subsequent chemistry.

The product of this reaction can be reacted with a suitable acid, such as HCl, at reflux, followed by reaction with cyanamide in a solvent such as N-methyl pyrrolidone with catalytic para-toluene sulfonic acid at elevated temperatures to provide 5-amino-8-(Ar)alkyl-2-(2-furyl)-pyrazolo[4,3-e]-1,2,4-triazolo[1,5c]pyrimidines.

These amine-substituted compounds can be reacted with appropriate isocyanates to form urea compounds, activated carboxylic acids such as acid halides to provide amides, activated sulfonic acids such as sulfonic acid halides to form sulfonamides, or other reactive carboxylic acid or sulfonic acid derivatives to form other desired compounds.

Triazolo-triazolo-pyrimidine compounds can be prepared using similar chemistry, but starting with a suitably functionalized azide, and reacting the azide with H$_2$NC(O)CH$_2$CN to form the initial heterocyclic ring, followed by reaction of the amide group with a dehydrating agent such as POCl$_3$ to form a nitrile. The resulting cyano-aminotriazole can be reacted in the same manner as the 3-cyano-2-aminopyrazoles discussed above to prepare triazolo-triazolo-pyrimidines.

Methods of Using the Compounds

The compounds can be used for all indications for which agonists and antagonists of the A3 receptor, including:
treating hypertension;
treating inflammatory disorders such as rheumatoid arthritis and psoriasis;
treating allergic disorders such as hay fever and allergic rhinitis;
mast cell degranulation;
antitumor agents;
treating cardiac hypoxia; and
protection against cerebral ischemia;
as described, for example, in Jacobson, TIPS May 1998, pp. 185–191, the contents of which are hereby incorporated by reference.

The compounds can be administered via any medically acceptable means. Suitable means of administration include oral, rectal, topical or parenteral (including subcutaneous, intramuscular and intravenous) administration, although oral or parenteral administration are preferred.

The amount of the compound required to be effective as an allosteric modulator of an adenosine receptor will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular compound to be administered. However, a suitable effective dose is in the range of about 0.1 μg/kg to about 10 mg/kg body weight per day, preferably in the range of about 1 mg/kg to about 3 mg/kg per day.

The total daily dose may be given as a single dose, multiple doses, e.g., two to six times per day, or by intravenous infusion for a selected duration. Dosages above or below the range cited above are within the scope of the present invention and may be administered to the individual patient if desired and necessary. For example, for a 75 kg mammal, a dose range would be about 75 mg to about 220 mg per day, and a typical dose would be about 150 mg per day. If discrete multiple doses are indicated, treatment might typically be 50 mg of a compound given 3 times per day.

Formulations

The compounds described above are preferably administered in formulation including an active compound, i.e., a compound of formula I, together with an acceptable carrier for the mode of administration. Suitable pharmaceutically acceptable carriers are known to those of skill in the art.

The compositions can optionally include other therapeutically active ingredients such as antivirals, antitumor agents, antibacterials, anti-inflammatories, analgesics, and immunosuppresants. The carrier must be pharmaceutically acceptable in the sense of being compatible with the other ingredients of the formulation and not deleterious to the recipient thereof.

The formulations can include carriers suitable for oral, rectal, topical or parenteral (including subcutaneous, intramuscular and intravenous) administration. Preferred carriers are those suitable for oral or parenteral administration.

Formulations suitable for parenteral administration conveniently include sterile aqueous preparation of the active compound which is preferably isotonic with the blood of the recipient. Thus, such formulations may conveniently contain distilled water, 5% dextrose in distilled water or saline. Useful formulations also include concentrated solutions or solids containing the compound of formula (I) which upon dilution with an appropriate solvent give a solution suitable for parental administration above.

For enteral administration, the compound can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

The compounds can also be administered locally by topical application of a solution, ointment, cream, gel, lotion or polymeric material (for example, a Pluronic™, BASF), which may be prepared by conventional methods known in the art of pharmacy. In addition to the solution, ointment, cream, gel, lotion or polymeric base and the active ingredient, such topical formulations may also contain preservatives, perfumes, and additional active pharmaceutical agents.

Formulations for rectal administration may be presented as a suppository with a conventional carrier, e.g., cocoa butter or Witepsol S55 (trademark of Dynamite Nobel Chemical, Germany), for a suppository base.

Alternatively, the compound may be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," *Drug Carriers in Biolopy and Medicine*, pp. 287–341 (Academic Press, 1979). Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474, 4,925, 673 and 3,625,214, the contents of which are hereby incorporated by reference.

Preferred microparticles are those prepared from biodegradable polymers, such as polyglycolide, polylactide and copolymers thereof. Those of skill in the art can readily determine an appropriate carrier system depending on various factors, including the desired rate of drug release and the desired dosage.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier and then, if necessary, shaping the product into desired unit dosage form.

In addition to the aforementioned ingredients, the formulations may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

Determination of the Degree of Activity for the Compounds

The activity of the compounds can be readily determined using no more than routine experimentation using any of the following assays.

Rat $A_1$ and $A_{2A}$ Adenosine Receptor Binding Assay

Membrane preparations:

Male Wistar rats (200–250 g) can be decapitated and the whole brain (minus brainstem, striatum and cerebellum) dissected on ice. The brain tissues can be disrupted in a Polytron (setting 5) in 20 vols of 50 mM Tris HCl, pH 7.4. The homogenate can then be centrifuged at 48,000 g for 10 min and the pellet resuspended in Tris-HCL containing 2 IU/ml adenosine deaminase, type VI (Sigma Chemical Company, St. Louis, Mo., USA). After 30 min incubation at 37° C., the membranes can be centrifuged and the pellets stored at −70° C. Striatal tissues can be homogenized with a Polytron in 25 vol of 50 mM Tris HCL buffer containing 10 mM $MgCl_2$ pH 7.4. The homogenate can then be centrifuged at 48,000 g for 10 min at 4° C. and resuspended in Tris HCl buffer containing 2 IU/ml adenosine deaminase. After 30 min incubation at 37° C., membranes can be centrifuged and the pellet stored at −70° C.

Radioligand binding assays:

Binding of [$^3$H]-DPCPX (1,3-dipropyl-8-cyclopentylxanthine) to rat brain membranes can be performed essentially according to the method previously described by Bruns et al., *Proc. Natl. Acad. Sci.* 77, 5547–5551 1980. Displacement experiments can be performed in 0.25 ml of buffer containing 1 nM [$^3$H]-DPCPX, 100 μl of diluted membranes of rat brain (100 μg of protein/assay) and at least 6–8 different concentrations of examined compounds. Non specific binding can be determined in the presence of 10 μM of CHA (N$^6$cyclohexyladenosine) and this is always ≦10% of the total binding. Incubation times are typically 120 min at 25° C.

Binding of [$^3$H]-SCH 58261 (5-amino-7-(2-phenylethyl)-2-(2-furyl)pyrazolo[4,3-e]-1,2,4-triazolo[1,5-c]pyrimidine) to rat striatal membranes (100 μg of protein/assay) can be performed according to methods described in Zocchi et al., *J. Pharm. and Exper. Ther.* 276:398–404 (1996). In competition studies, at least 6–8 different concentrations of examined compounds should be used. Non specific binding can be determined in the presence of 50 μM of NECA (5'-(N-ethylcarboxamido)adenosine). Incubation time is typically 60 min at 25° C.

Bound and free radioactivity can be separated by filtering the assay mixture through Whatman GF/B glass-fiber filters using a Brandel cell harvester (Gaithersburg, Md., USA). The incubation mixture can be diluted with 3 ml of ice-cold incubation buffer, rapidly vacuum filtered and the filter can be washed three times with 3 ml of incubation buffer. The filter bound radioactivity can be measured, for example, by liquid scintillation spectrometry. The protein concentration can be determined, for example, according to a Bio-Rad method (Bradford, *Anal. Biochem.* 72:248 (1976)) with bovine albumin as reference standard.

Human cloned A$_3$ Adenosine Receptor Binding Assay

Receptor binding assays:

Binding assays can be carried out according to methods described in Salvatore et al., *Proc. Natl. Acad. Sci.* 90:10365–10369 (1993). In saturation studies, an aliquot of membranes (8 mg protein/ml) from HEK-293 cells transfected with the human recombinant A$_3$ adenosine receptor (Research Biochemical International, Natick, Mass. USA) can be incubated with 10–12 different concentrations of [$^{125}$I]AB-MECA ranging from 0.1 to 5 nM. Competition experiments can be carried out in duplicate in a final volume of 100 μl in test tubes containing 0.3 nM [$^{125}$I]AB-MECA, 50 mM Tris HCL buffer, 10 mM MgCl$_2$, pH 7.4 and 20 μl of diluted membranes (12.4 mg protein/ml) and at least 6–8 different concentrations of examined ligands. Incubation time was 60 min at 37° C., according to the results of previous time-course experiments. Bound and free radioactivity were separated by filtering the assay mixture through Whatiman GF/B glass-fiber filters using a Brandel cell harvester. Non-specific binding was defined as binding in the presence of 50 μM R-PIA and was about 30% of total binding. The incubation mixture was diluted with 3 ml of ice-cold incubation buffer, rapidly vacuum filtered and the filter was washed three times with 3 ml of incubation buffer. The filter bound radioactivity was counted in a Beckman gamma 5500B γ counter. The protein concentration can be determined according to a Bio-Rad method (3) with bovine albumin as reference standard.

Data Analysis

Inhibitory binding constant, K$_i$, values can be calculated from those of I C$_{50}$ according to the Cheng & Prusoff equation (Cheng and Prusoff, *Biochem. Pharmacol.* 22:3099–3108 (1973)), K$_i$=IC$_{50}$/(I+[C*]/K$_D$*), where [C*] is the concentration of the radioligand and K$_D$* its dissociation constant.

A weighted non linear least-squares curve fitting program LIGAND (Munson and Rodbard, *Anal. Biochem.* 107:220–239 (1990)) can be used for computer analysis of saturation and inhibition experiments. Data are typically expressed as geometric mean, with 95% or 99% confidence limits in parentheses.

EXAMPLES

The following examples illustrate aspects of this invention but should not be construed as limitations. The symbols and conventions used in these examples are intended to be consistent with those used in the contemporary, international, chemical literature, for example, the *Journal of the American Chemical Society* ("*J.Am.Chem.Soc.*") and *Tetrahedron*.

Example 1

Preparation of 8-(Ar)alkyl-2-(2-furyl)-pyrazolo[4,3-e]]1,2,4-triazolo[1,5-c]pyrimidines (Compounds 18–25)

8-(Ar)alkyl-2-(2-furyl)-pyrazolo[4,3-e]1,2,4-triazolo[1,5-c]pyrimidines were prepared according to the synthetic strategy shown in the following Scheme VI.

Scheme VI

General procedures for the preparation of 8-(Ar)alkyl-2-(2-furyl)-pyrazolo[4,3-e]1,2,4-triazolo[1,5-c]pyrimidine (18–25)

Reagents: a) NaH, DMF, R$^2$X; b) HC(OEt)$_3$, reflux; c) 2-Furoic hydrazide, MeO(CH$_2$)$_2$OH; d) Ph$_2$O, 260° C., flash chromatography

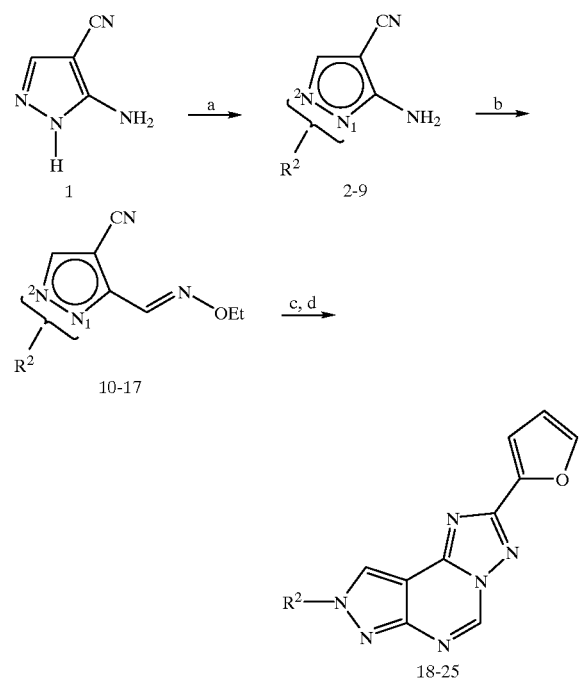

In the preparation of compounds 18–25, a solution of 1 (10 mmol) in 40 ml of DMF cooled to 0° C. was treated with NaH (60% in oil, 12 mmol) in several portions over 10 minutes. After 45 minutes, the appropriate (ar)alkyl halide (12 mmol), was added and the reaction mixture was allowed to warm to 25° C. and stirred for 3–5 h (TLC: EtOAc 1:1). The reaction was quenched by addition of $H_2O$ (80 ml), and the aqueous layer was extracted with EtOAc (5×25 ml). The organic layers were recombined, dried ($Na_2SO_4$), filtered and concentrated at reduced pressure, to afford the alkylated pyrazole (2–9) as inseparable mixture of $N^1$ and $N^2$ isomers (ratio approximately 1:4). This mixture of $N^1$ and $N^2$-substituted-4-cyano-5-amino pyrazoles (2–9) was then dissolved in triethyl orthoformate (60 ml) and the solution was refluxed under nitrogen for 8 h. The solvent was then removed under vacuum and the oily residue constituted by the mixture of imidates (10–17) was dissolved in 2-methoxyethanol (50 ml) and 2-furoic acid hydrazide (13 mmol) was added. The mixture was refluxed for 5–10 h, then, after cooling, the solvent was removed under reduced pressure and the dark oily residue was cyclized further any other purification in diphenyl ether (50 ml) at 260° C. using a Dean-Stark apparatus for the azeotropic elimination of water produced in the reaction. After 1.5 h, the mixture was cooled and poured onto hexane (300 ml). The precipitate was collected by filtration and purified by chromatography (EtOAc/hexane 1:1). In this way, the major product ($N^8$ alkylated) (18–25) was obtained in a good overall yield.

Following this general procedure the following compounds have been prepared:

8-Methyl-2-(2-furyl)-pyrazolo[4,3-e]1,2,4-triazolo[1,5-c]pyrimidine (18)

yield 45%; yellow solid, m.p. 155–156° C. (EtOAc-light petroleum); IR (KBr): 1615, 1510 cm$^{-1}$; $^1$H NMR (DMSO d$_6$) δ 4.1 (s, 1H); 6.32 (m, 1H); 7.25 (m, 1H); 8.06 (m, 1H); 8.86 (s, 1H), 9.38 (s, 1H).

8-Ethyl-2-(2-furyl)-pyrazolo[4,3-e]1,2,4-triazolo[1,5-c]pyrimidine (19)

yield 50%; pale yellow solid m.p. 188–189° C. (EtOAc-light petroleum); IR (KBr): 1620, 1500 cm$^{-1}$; $^1$H NMR (DMSO d$_6$) δ 1.67 (t, 2H, J=7); 4.53 (q, 2H, J=7); 6.59 (m, 1H); 7.23 (m, 1H); 7.64 (s, 1H); 8.34 (s, 1H); 9.10 (s, 1H).

8-Propyl-2-(2-furyl)-pyrazolo[4,3-e]1,2,4-triazolo[1,5-c]pyrimidine (20)

yield 60%; yellow solid m.p. 189–190° C. (EtOAc-light petroleum); IR (KBr): 1600, 1505 cm$^{-1}$; $^1$H NMR (DMSO d$_6$) δ 0.98 (t, 2H, J=7); 2.03–2.10 (m, 2H); 4.41 (q, 2H, J=7); 6.60 (m, 1H); 7.24 (m, 1H); 7.64 (s, 1H); 8.32 (s, 1H); 9.10 (s, 1H).

8-Butyl-2-(2-furyl)-pyrazolo[4,3-e]1,2,4-triazolo[1,5-c]pyrimidine (21)

yield 50%, pale yellow solid m.p. 245–247° C. (EtOAc-light petroleum); IR (KBr): 1610, 1500 cm$^{-1}$; $^1$H NMR (DMSO d$_6$) δ 0.9 (m, 3H); 1.3 (m, 2H); 1.9 (m, 2H); 4.5 (t, 2H, J=7.2); 6.2 (m, 1H); 7.3 (m, 1H); 8.0 (m, 1H); 8.9 (s, 1H); 9.4 (s, 1H).

8-Isopentyl-2-(2-furyl)-pyrazolo[4,3-e]1,2,4-triazolo[1,5-c]pyrimidine (22)

yield 54%; pale yellow solid m.p. 235–237° C. (EtOAc-light petroleum); IR (KBr): 1635, 1510, 1450 cm$^{-1}$; $^1$H NMR (DMSO d$_6$) δ 1.0 (d, 6H, J=6.2); 1.5–1.9 (m, 3H); 4.6 (t, 2H, J=7.4); 6.6 (m, 1H), 7.3 (m, 1H); 7.7 (m, 1H); 8.8 (s, 1H); 9.1 (s, 1H).

8-(2-Isopentenyl)-2-(2-furyl)-pyrazolo[4,3-e]1,2,4-triazolo[1,5-c]pyrimidine (23)

yield 48%; yellow solid map 210–212° C. (EtOAc-light petroleum); IR (KBr): 1625, 1500, 1430 cm$^{-1}$; $^1$H NMR (DMSO d$_6$) δ 1.79 (s, 3H); 1.87 (s, 3H); 1.87 (s, 3H); 5.05 (d, 2H, J=6); 5.55–5.63 (m, 1H); 6.60 (m, 1H); 7.24 (m, 1H); 7.64 (s, 1H) 8.34 (s, 1H); 9.10 (s, 1H).

8-2-Phenylethyl-2-(2-furyl)-pyrazolo[4,3-e]1,2,4-triazolo[1,5-c]pyrimidine (24)

yield 56%, m.p. 268–270° C.; (EtOAc-Light petroleum); IR (KBr): 1660, 1510, 1450 cm$^{-1}$; $^1$H NMR (DMSO d$_6$) δ 3.32 (t, 2H, J=6.7); 4.72 (t, 2H, J=6.7); 6.73 (s, 1H); 7.23 (m, 5H); 7.95 (s, 1H); 8.8 (s, 1H); 9.41 (s, 1H). Anal. ($C_{18}H_{14}N_6O$) C, H, N.

8-(3-phenylpropyl)-2-(2-furyl)-pyrazolo[4,3-e]1,2,4-triazolo[1,5-c]pyrimidine (25)

yield 63%; yellow solid m.p. 165–166° C. (EtOAc-light petroleum); IR (KBr): 1630, 1500, 1440 cm$^{-1}$; $^1$H NMR (DMSO d$_6$) δ 2.34–2.48 (m, 2H); 2.67 (t, 3H, J=7.5); 4.43 (t, 2H, J=7.5), 6.61 (m, 1H); 7.16–7.32 (m, 6H); 7.64 (d, 1H, J=2); 8.29 (s, 1H); 9.02 (s, 1H).

Example 2

Preparation of 5-Amino-8-(ar)alkyl-2-(2-furyl)-pyrazolo[4,3-e]1,2,4-triazolo[1,5-c]pyrimidines (Compounds 33–40)

5-Amino-8-(ar)alkyl-2-(2-furyl)-pyrazolo[4,3-e]1,2,4-triazolo[1,5-c]pyrimidines can be prepared according to the synthetic strategy shown in the following Scheme VII.

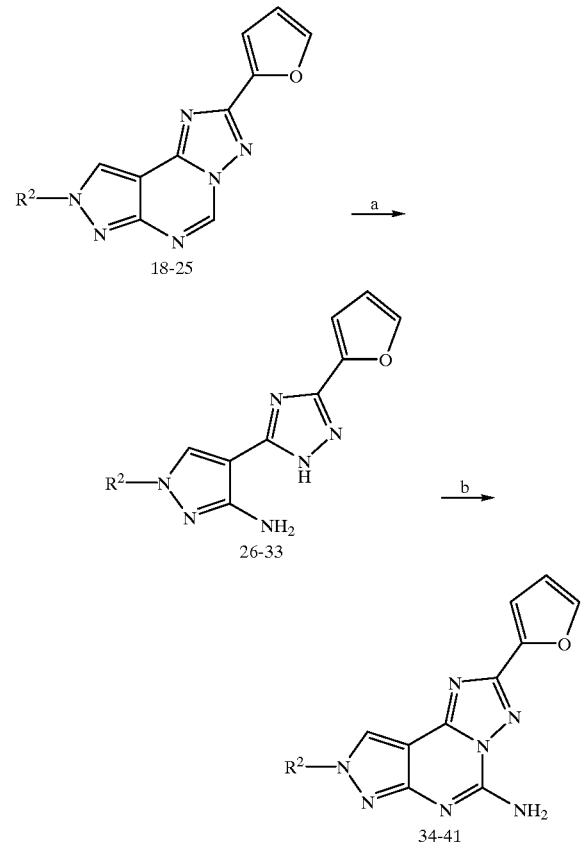

Scheme VII

General procedures for the preparation of 5-Amino-8-(ar)alkyl-2-(2-furyl)-pyrazolo[4,3-e]1,2,4-triazolo[1,5-c]pyrimidine (33–40)

Reagents: a) HCl, reflux; b) $NH_2CN$, 1-methyl-2-pyrrolidone, pTsOH, 140° C.

In the preparation of compounds 33–40, a solution of the mixture of triazolo-pyrimidine (18–25) (10 mmol) in aqueous 10% HCl (50 ml) was refluxed for 3 h. Then the solution was cooled and neutralized with a saturated solution of $N_aHCO_3$ at 0° C. The compounds (26–33) were extracted with EtOAc (3×20 ml), the organic layers were dried with $Na_2SO_4$ and evaporated under vacuum. The obtained crude amine (26–33) was dissolved in N-methyl pyrrolidone (40 ml), cyanamide (60 mmol) and p-toluene sulfonic acid (15 mmol) were added and the mixture was heated at 160° C. for 4 h. Then cyanamide (60 mmol) was added again and the solution was heated overnight. Then the solution was diluted with EtOAc (80 ml) and the precipitate (excess of cyanamide) was collected by filtration; the filtrate was concentrated under reduced pressure and washed with water (3×30 ml). The organic layer was dried ($Na_2SO_4$) and evaporated under vacuum. The residue was purified by chromatography (EtOAc/light petroleum 2:1) to afford the desired product (34–41) as a solid, Following this general procedure the following compounds have been prepared:

5-Amino-8-methyl-2-(2-furyl)-pyrazolo[4,3-e]1,2,4-triazolo[1,5-c]pyrimidine (34)

yield 53%; yellow solid m.p. 167–168° C. (EtOAc-light petroleum); IR (KBr): 3500–2950, 1680, 1645, 1610, 1560, 1455 cm$^{-1}$; 1H NMR (DMSO d$_6$) δ 4.12 (s, 3H); 6.70 (m, 1H); 6.99 (bs, 2H); 7.18 (m, 1H); 7.81 (s, 1H), 8.42 (s, 1H).

5-Amino-8-ethyl-2-(2-furyl)-pyrazolo[4,3-e]1,2,4-triazolo[1,5-c]pyrimidine (35)

yield 65%, yellow solid m.p. 249–250° C. (EtOAc-light petroleum); IR (KBr): 3430–2950, 1680, 1655, 1620, 1550, 1450 cm$^{-1}$; $^1$H NMR (DMSO d$_6$) δ 1.46 (t, 2H, J=7); 4.30 (d, 2H, J=7); 6.72 (m, 1H); 7.18 (m, 1H); 7.93 (bs, 2H); 7.93 (s, 1H); 8.62 (s, 1H).

5-Amino-8-propyl-2-(2-furyl)-pyrazolo[4,3-e]1,2,4-triazolo[1,5-c]pyrimidine (36)

yield 57%; pale yellow solid m.p. 209–210° C. (EtOAc-light petroleum); IR (KBr): 3400–2900, 1660, 1645, 1610, 1545, 1430 cm$^{-1}$; $^1$H NMR (DMSO d$_6$) δ 0.83 (t, 2H, J=7); 1.81–1.91 (m, 2H); 4.22 (d, 2H, J=7); 6.71 (m, 1H); 7.19 (m, 1H); 7.63 (bs, 2H); 7.93 (s, 1H); 8.61 (s, 1H).

5-Amino-8-butyl-2-(2-furyl)-pyrazolo[4,3-e]1,2,4-triazolo[1,5-c]pyrimidine (37)

yield 47%; white solid m.p. 200–203° C. (EtOAc-light petroleum); IR (KBr): 3500–2900, 1685, 1640, 1620, 1550, 1450 cm$^{-1}$; $^1$H NMR (DMSO d$_6$) δ 0.9 (t, 3H); 1.2 (m, 2H); 1.8 (m, 2H); 4.2 (t, 2H); 6.7 (m, 1H); 7.2 (m, 2H); 7.6 (s, 1H); 8.0 (s, 1H); 8.6 (s, 1H).

5-Amino-8-isopentyl-2-(2-furyl)-pyrazolo[4,3-e]1,2,4-triazolo[5-c]pyrimidine (38)

yield 60%; off-white solid m.p. 212–213° C. (EtOAc-light petroleum); IR (KBr): 3500–2850, 1670, 1650, 1615, 1560, 1455 cm$^{-1}$; 1H NMR (CDCl$_3$) δ 0.96 (d, 6H, J=6.4); 1.59 (m, 1H); 1.86 (m, 2H); 4.32 (t, 2H, J=6.4); 6.58 (m, 1H); 6.72 (bs, 2H); 7.21 (d, 1H, J=4.2); 7.63 (d, 1 H, J=1.2); 8.10 1H).

5-Amino-8-(2-isopentenyl)-2-(2-furyl)-pyrazolo[4,3-e]1,2,4-triazolo[1,5-c]pyrimidine (39)

yield 58%; pale yellow solid m.p. 178–179° C. (EtOAc-light petroleum); IR (KBr): 3520–2950, 1665, 1640, 1610, 1555, 1450 cm$^{-1}$; $^1$H NMR (CDCl$_3$) δ 1.74 (s, 3H); 1.77 (s, 3H); 4.87 (d, 2H, J=7); 5.43–5.46 (m, 1H); 6.72 (m, 1H); 7.18 (m, 1H); 7.62 (bs, 2H); 7.93 (s, 1H); 8.55 (s, 1H).

5-Amino-8-(2-phenylethyl)-2-(2-furyl)-pyrazolo[4,3-e]1,2,4-triazolo[1,5-c]pyrimidine (40)

yield 45%; white solid m.p. 183–185° C. (EtOAc-light petroleum); IR (KBr): 3500–2900, 1670, 1645, 1620, 1530, 1455 cm$^{-1}$; $^1$H NMR (DMSO d$_6$) δ 3.21 (t, 2H, J=6.4); 4.53 (t, 2H, J=6.4); 6.7 (s, 1H); 7.1–7.4 (m, 6H), 7.65 (bs, 2H); 7.93 (s,1H); 8.45 (s, 1H).

5-Amino-8-(3-phenylpropyl)-2-(2-furyl)-pyrazolo[4,3-e]1,2,4-triazolo[1,5-c]pyrimidine (41)

yield 57%; yellow solid m.p. 168–170° C. (EtOAc-light petroleum); IR (KBr): 3510–2950, 1665, 1640, 1615, 1520, 1455 cm$^{-1}$; 1H NMR (DMSO d$_6$) δ 2.14–2.21 (m, 2H); 2.54 (t, 2H, J=7); 4.29 (t, 2H, J=6.4); 6.71 (s, 1H); 7.14–7.32 (m, 6H), 7.64 (bs, 2H); 7.93 (s, 1H); 8.64 (s, 1H).

Example 3

Preparation of 5-[[(Substituted phenyl)amino]carbonyl]amino-8-(ar)alkyl-2-(2-furyl)-pyrazolo[4,3-e]1,2,4-triazolo[1,5-c]pyrimidine (Compounds 42–57)

5-[[substituted phenyl)carbonyl]amino-8-(Ar)alkyl-2-(2-furyl)-pyrazolo]4,3-e]1,2,4-triazolo[1,5-c]pyrimidines can be prepared according to the synthetic strategy shown in the following Scheme VIII.

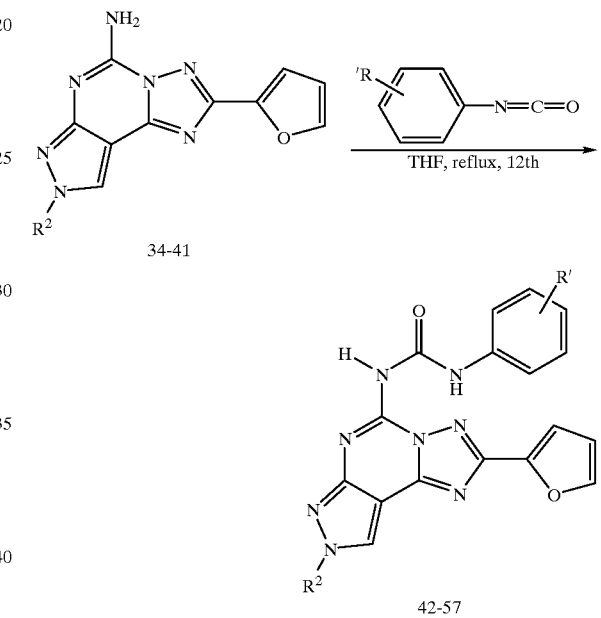

Scheme VIII

General Procedures for the Preparation of 5-[[(Substituted phenyl)amino]carbonyl]amino-8-(ar)alkyl-2-(2-furyl)-pyrazolo[4,3-e]1,2,4-triazolo[1,5-c]pyrimidine (42–57)

In the preparation of compounds 42–57, the appropriate amino compound (34–41) (10 mmol) was dissolved in freshly distilled THF (15 ml) and the appropriate isocyanate (13 mmol) was added. The mixture was refluxed under argon for 18 hours. Then the solvent was removed under reduced pressure and the residue was purified by flash chromatography (EtOAc-light petroleum 4–6) to afford the desired compounds 42–57. Following this general procedure the following compounds have been prepared:

5-[[(3-Chlorophenyl)amino]carbonyl]amino-8-methyl-2-(2-furyl)-pyrazolo[4,3-e]1,2,4-triazolo[1,5-c]pyrimidine (42)

yield 98%; pale yellow solid m.p. 142–145° C. (Et$_2$-light petroleum); I (KBr): 3210–2930, 1660, 1630, 1610, 1500 cm$^{-1}$; $^1$H NMR (CDCl$_3$) δ 4.21 (s, 3H); 6.60 (m, 1H); 7.11 (d, 1H, J=8); 7.13–7.28 (m, 2H): 7.55 (d, 1H, J=8); 7.65 (s, 1H); 7.78 (d, 1H, J=2); 8.22 (s, 1H); 8.61 (bs, 1H); 11.24 (bs, 1H).

5-[[(4-Methoxyphenyl)amino]carbonyl]amino-8-methyl-2-(2-furyl)-pyrazolo[4,3-e]1,2,4-triazolo[1,5-c]pyrimidine (43)

yield 99%; yellow solid m.p. 193–195° C. (Et$_2$O-light petroleum); IR (KBr): 3200–2900, 1664, 1625, 1600, 1500 cm$^{-1}$, 1H NMR (CDCl$_3$) δ 3.81 (s, 3H); 4.20 (s, 3H); 6.61 (m, 1H); 6.85 (d, 2H, J=9); 7.26 (m, 1H); 7.55 (d, 2H, J=9); 7.65 (s, 1H); 8.21 (s, 1H); 8.59 (bs, 1H); 10.96 (bs, 1H).

5-[[(3-Chlorophenyl)amino]carbonyl]amino-8-ethyl-2-(2-furyl)-pyrazolo[4,3-e]1,2,4-triazolo[1,5-c]pyrimidine (44)

yield 98%; pale yellow solid m.p. 204–205° C. (Et$_2$O-light petroleum); IR (KBr): 3220–2930, 1660, 1620, 1600, 1500 cm$^{-1}$; $^1$H NMR (CDCl$_3$) δ 1.71 (t, 3H, J=7); 4.50 (q, 2H, J=7); 6.67 (m, 1H); 7.20 (d, 1H, J=8); 7.31 (m, 1H); 7.61 (d, 1H, J=8); 7.70 (s, 1H); 7.84 (s, 1H); 8.30 (s, 1H); 8.67 (bs, 1H); 11.30(bs, 1H).

5-[[(4-Methoxyphenyl)amino]carbonyl]amino-8-ethyl-2-(2-furyl)-pyrazolo[4,3-e]1,2,4-triazolo[1,5-c]pyrimidine (45)

yield 99%; pale yellow solid m.p. 200–201° C. (Et$_2$O-light petroleum); IR (KBr): 3250–2950, 1665, 1620, 1610, 1520 cm$^{-1}$; $^1$H NMR (CDCl$_3$) δ 1.71 (t, 3H, J=7); 3.85 (s, 3H); 4.49 (s, 3H); 6.65 (m, 1H); 6.88 (d, 2H, J=9); 7.26 (m, 1H); 7.58 (d, 2H, J=9); 7.69 (s, 1H); 8.28 (s, 1H); 8.63 (bs, 1H); 10.99 (bs, 1H).

5-[[(3-Chlorophenyl)amino]carbonyl]amino-8-propyl-2-(2-furyl)-pyrazolo[4,3-e]1,2,4-triazolo[1,5-c]pyrimidine (46)

yield 95%; white solid m.p. 138–139° C. (Et$_2$O-light petroleum): IR (KBr): 3210–2920, 1655, 1615, 1600, 1510 cm$^{-1}$; $^1$H NMR (CDCl$_3$) δ 1.71 (t, 3H, J=7); 2.04 (m, 2H); 4.36 (q, 2H, J=7); 6.62 (m, 1H); 7.12 (d, 1H, J=8); 7.27 (m, 1H); 7.56 (d, 1H, J=8); 7.66 (s, 1H); 7.80 (s, 1H); 8.24 (s, 1H); 8.62 (bs, 1H); 11.08 (bs, 1H).

5-[[(4-Methoxyphenyl)amino]carbonyl]amino-8-propyl-2-(2-furyl)-pyrazolo[4,3-e]1,2,4-triazolo[1,5-c]pyrimidine (47)

yield 98%; pale yellow solid m.p. 146–148° C. (Et$_2$O-light petroleum); IR (KBr): 3230–2950, 1660, 1620,1600, 1530 cm$^{-1}$; $^1$H NMR (CDCl$_3$) δ 0.98 (t, 3H, J=7); 2.04–2.08 (m, 2H); 3.82 (s, 3H); 4.35 (t, 2H, J=7); 6.61 (m, 1H); 6.89 (d, 2H, J=9); 7.25 (m, 1H); 7.56 (d, 2H, J=9); 7.65 (s, 1H); 8.23 (s, 1H); 8.59 (bs, 1H); 10.95 (bs, 1H).

5-[[(3-Chlorophenyl)amino]carbonyl]amino-8-butyl-2-(2-furyl)-pyrazolo[4,3-e]1,2,4-triazolo[1,5-c]pyrimidine (48)

yield 97%; white solid m.p. 210–212° C. (Et$_2$O-light petroleum); IR (KBr): 3240–2970, 1650, 1610, 1510 cm$^{-1}$; $^1$H NMR (CDCl$_3$) δ 1.00 (t, 3H, J=7); 1.39–1.41 (m, 2H); 1.99–2.03 (m, 2H); 4.41 (q, 2H, J=7); 6.63 (m, 1H); 7.14 (d, 1H, J=8); 7.29 (m, 1H); 7.56 (d, 1H, J=8); 7.67 (s, 1H), 7.80 (s, 1H); 8.25 (s, 1H); 8.63 (bs, 1H); 11.26 (bs, 1H).

5-[[(4-Methoxyphenyl)amino]carbonyl]amino-8-butyl-2-(2-furyl)-pyrazolo[4,3-e]1,2,4-triazolo[1,5-c]pyrimidine (49)

yield 96%; white solid m.p. 197–198° C. (Et$_2$O-light petroleum); IR (KBr): 3250–2960, 1665, 1610, 1600, 1520 cm$^{-1}$; $^1$H NMR (CDCl$_3$) δ 0.98 (t, 3H, J=7); 1.38–1.42 (m, 2H); 2.02–2.05 (m, 2H); 3.82 (s, 3H); 4.39 (t, 2H, J=7); 6.63 (m, 1H); 6.92 (d, 2H, J=9); 7.25 (m, 1H); 7.57 (d, 2H, J=9); 7.67 (s, 1H); 8.23 (s, 1H); 8.60 (bs, 1H); 10.95 (bs, 1H).

5-[[(3-Chlorophenyl)amino]carbonyl]amino-8-isopentyl-2-(2-furyl)-pyrazolo[4,3-e]1,2,4-triazolo[1,5-c]pyrimidine (50)

yield 97%; pale yellow solid m.p. 199–200° C. (Et$_2$O-light petroleum); IR (KBr): 3230–2950, 1655, 1600, 1510 cm$^{-1}$; $^1$H NMR (CDCl$_3$) δ 1.01 (d, 6H, J=7.5); 1.49–1.51 (m, 1H); 1.88–2.03 (m, 2H); 4.42 (t, 2H, J=7); 6.62 (m, 1H); 7.13 (d, 1H, J=8); 7.34 (m, 1H); 7.57 (d, 1H, J=8); 7.67 (s, 1H); 7.80 (s, 1H); 8.24 (s, 1H); 8.63 (bs, 1H); 11.25 (bs, 1H).

5-[[(4-Methoxyphenyl)amino]carbonyl]amino-8-isopentyl-2-(2-furyl)-pyrazolo[4,3-e]1,2,4-triazolo[1,5-c]pyrimidine (51)

yield 98%; white solid m.p. 192–193° C. (Et$_2$O-light petroleum); IR (KBr): 3230–2970, 1660, 1615, 1600, 1500 cm$^{-1}$; $^1$H NMR (CDCl$_3$) δ 0.99 (d, 6H, J=7.5); 1.58–1.22 (m, 1H); 1.87–1.97 (m, 2H); 3.82 (s, 3H); 4.40 (t, 2H, J=7); 6.62 (m, 1H); 6.91 (d, 2H, J=9); 7.23 (m, 1H); 7.58 (d, 2H, J=9); 7.66 (s, 1H); 8.23 (s, 1H); 8.59 (bs, 1H); 10.94 (bs, 1H).

5-[[(3-Chlorophenyl)amino]]carbonyl]amino-8-(2-isopentenyl)-2-(2-furyl)pyrazolo[4,3-e]1,2,4-triazolo[1,5-c]pyrimidine (52)

yield 99%; white solid m.p. 204–205° C. (Et$_2$O-light petroleum); IR (KBr): 3245–2960, 1650, 1600, 1510 cm$^{-1}$, $^1$H NMR (CDCl$_3$) δ 1.84 (s, 3H); 1.88 (s, 3H); 5.01 (d, 2H, J=8); 5.57 (m, 1H); 6.62 (m, 1H); 7.12 (d, 1H, J=8); 7.29 (m, 1H); 7.56 (d, 1H, J=8); 7.66 (s, 1H); 7.80 (s, 1H); 8.26 (s, 1H); 8.60 (bs, 1H); 11.26 (bs, 1H).

5-[[(4-Methoxyphenyl)amino]carbonyl]amino-8-(2-isopentenyl)-2-(2-furyl)-pyrazolo[4,3-e]1,2,4-triazolo[1,5-c]pyrimidine (53)

yield 96%; pale yellow solid m.p. 198–199° C. (Et$_2$O-light petroleum); IR (KBr): 3235–2950, 1665, 1620, 1600, 1510 cm$^-$, $^1$H NMR (CDCl$_3$) δ 1.83 (s, 3H); 1.87 (s, 3H); 3.81 (s, 3H); 4.97 (d, 2H, J=7); 5.57 (m, 1H); 6.61 (m, 1H); 6.93 (d, 2H, J=9); 7.24 (m, 1H); 7.54 (d, 2H, J=9); 7.66 (s, 1H); 8.25 (s, 1H); 8,58 (bs, 1H); 10.96 (bs, 1H).

5-[[(3-Chlorophenyl)amino]carbonyl]amino-8-(2-phenylethyl)-2-(2-furyl)-pyrazolo[4,3-e]1,2,4-triazolo[1,5-c]pyrimidine (54)

yield 98%; white solid m.p. 186–187° C. (Et$_2$O-light petroleum); IR (KBr): 3250–2970, 1660, 1610, 1515 cm$^{-1}$; $^1$H NMR (CDCl$_3$) δ 3.33 (t, 2H, J=7); 4.62 (t, 2H, J=7); 6.60 (m, 1H); 7.19–7.35 (m, 7H); 7.57 (d, 1H, J=8); 7.61 (s, 1H); 7.81 (s, 1H); 7.89 (s, 1H); 8.63 (bs, 1H); 11.27 (bs, 1H).

5-[[(4-Methoxyphenyl)amino]carbonyl]amino-8-(2-phenylethyl)-2-(2-furyl)-pyrazolo[4,3-e]1,2,4-triazolo[1,5-c]pyrimidine (55)

yield 99%; white solid m.p. 180–181° C. (Et$_2$O-light petroleum); IR (KBr); 3245–2960, 1660, 1615, 1600, 1500 cm$^{-1}$; $^1$H NMR (CDCl$_3$) δ 3.42 (t, 2H, J=7); 3.82 (s, 3H); 4.60 (t, 2H, J=7); 6.60 (m, 1H); 6.93 (d, 2H, J=9); 7.09 (m, 2H); 7.20–7.28 (m, 4H); 7.56 (d, 2H, J=8); 7.60 (s, 1H); 7.89 (s, 1H); 8.59 (bs, 1H); 10.96 (bs, 1H).

5-[[(3-Chlorophenyl)amino]carbonyl]amino-8-(3-phenylpropyl)-2-(2-furyl)-pyrazolo[4,3-e]1,2,4-triazolo[1,5-c]pyrimidine (56)

yield 99%; pale yellow solid m.p. 183–184° C. (Et$_2$O-Light petroleum); IR (KBr); 3245–2960, 1665, 1610, 1515 cm$^-$, $^1$H NMR (CDCl$_3$) δ 2.46 (m, 2H); 2.73 (t, 2H, J=7); 4.43 (t, 2H, J=7); 6.66 (m, 1H); 7.19–7.40 (m, 8H); 7.59 (d, 1H, J=8); 7.64 (s, 1H); 7.85 (m, 1H); 8.25 (s, 1H); 8.67 (bs, 1H); 11.30 (bs, 1H).

5[[(4-Methoxyphenyl)amino]carbonyl]amino-8-(3-phenylpropyl)-2-(2-furyl)-pyrazolo[4,3-e]1,2,4-triazolo[1,5-c]pyrimidine (57)

yield 98%; white solid m.p. 174–175° C. (Et$_2$O-light petroleum); IR (KBr): 3240–2950, 1665, 1615, 1600, 1510 cm$^{-1}$; $^1$H NMR (CDCl$_3$) δ 2.46 (m, 2H); 2.73 (t, 2H, J=7); 4.42 (t, 2H, J=7); 6.67 (m, 1H); 6.96 (d, 2H, J=9); 7.22–7.41 (m, 6H); 7.60 (d, 2H, J=8); 7.64 (s, 1H); 8.25 (s, 1H), 8.65 (bs, 1H); 11.16 (bs, 1H).

Example 4

Preparation of 5-[(Benzyl)carbonyl]amino-8-(ar)alkyl-2-(2-furyl)-pyrazolo[4,3-e]1,2,4-triazolo[1,5-c]pyrimidine (Compounds 58–59)

5-[[benzyl)carbonyl]amino-8-(Ar)alkyl-2-(2-furyl)-pyrazolo[4,3-e]1,2,4-triazolo[1,5-c]pyrimidines can be prepared according to the synthetic strategy shown in the following Scheme IX.

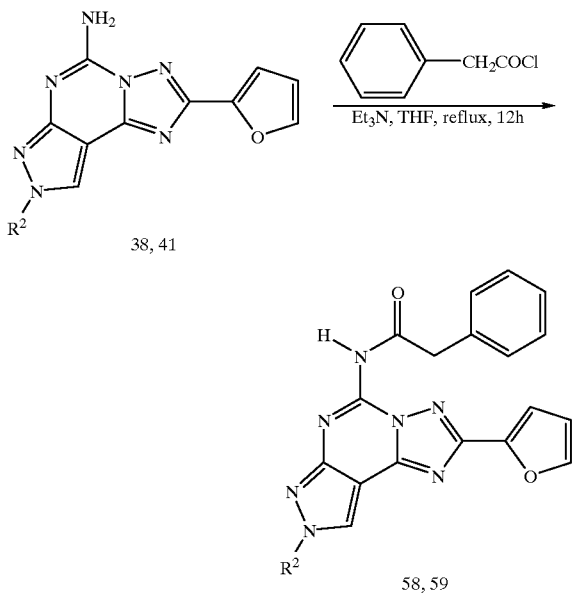

Scheme IX

General Procedures for the Preparation of 5-[(Benzyl)carbonyl]amino-8-(ar)alkyl-2-(2-furyl)-pyrazolo[4,3-e]1,2,4-triazolo[1,5-c]pyrimidine (58–59)

In the preparation of compounds 58–59, the appropriate amino compound (38 or 41) (10 mmol) was dissolved in freshly distilled THF (15 ml) and the appropriate acid halide (13 mmol) and triethylamine (13 mmol) were added. The mixture was refluxed under argon for 18 hours. The solvent was then removed under reduced pressure and the residue was dissolved in EtOAc (30 ml) and washed twice with water (15 ml). The organic phase was dried on $Na_2SO_4$ and concentrated under reduced pressure. The residue was purified by flash chromatography (EtOAc-light petroleum 4:6) to afford the desired compounds 58, 59. Following this general procedure the following compounds have been prepared:

5-[(Benzyl)carbonyl]amino-8-isopentyl-2-(2-furyl)-pyrazolo[4,3-e]1,2,4-triazolo[1,5-c]pyrimidine (58)

yield 85%, pale yellow solid m.p. 144–145° C. ($Et_2O$-light petroleum); IR (KBr): 3255–2930, 1673, 1620, 1610, 1520 $cm^{-1}$; $^1H$ NMR ($CDCl_3$) δ 0.98 (d, 6H, J=7.5); 1.60 (m, 1H); 1.91 (m, 1H); 4.40 (t, 2H, J=7); 4.53 (s, 2H); 6.60 (m, 1H); 7.18 (m, 1H); 7.26–7.39 (m, 5H); 7.64 (s, 1H); 8.22 (s, 1H); 9.11 (bs, 1H).

5-[(Benzyl)carbonyl]amino-8-(3-phenylpropyl)-2-(2-furyl)-pyrazolo[4,3-e]2,4-triazolo[1,5-c]pyrimidine (59)

yield 95%, pale yellow solid m.p. 116–117° C. ($Et_2O$-light petroleum); IR (KBr); 3250–2900, 1675, 1625, 1600, 1500 $cm^{-1}$; $^1H$ NMR ($CDCl_3$) δ 2.39 (m, 2H); 2.67 (t, 2H, J=7); 4.37 (t, 2H, J=7); 4.53 (s, 2H); 6.61 (m, 1H); 7.16–7.43 (m, 11H); 7.65 (s, 1H); 7.64 (s, 1H); 8.19 (s, 1H); 9.12 (bs, 1H).

Example 5

Preparation of 1-Substituted-4-cyano-5-aminopyrazoles

According to the procedures described in *J. Org. Chem.* 1956, 21, 1240; *J. Am. Chem. Soc.* 1956, 78, 784 and the references herein cited, the following compounds are prepared, starting from commercially available ethoxy methylene malonodinitrile and N1-substituted hydrazines, which also are mainly commercially available:

1-methyl-4-cyano-5-aminopyrazole
1-n-butyl-4-cyano-5-aminopyrazole
1-isopentyl-4-cyano-5-aminopyrazole
1-(2-cyclopentyl)ethyl-4-cyano-5-aminopyrazole
1-hydroxyethyl-4-cyano-5-aminopyrazole
1-phenyl-4-cyano-5-aminopyrazole
1-tert-butyl-4-cyano-5-aminopyrazole.
1-phenylethyl-4-cyano-5-aminopyrazole
1-(2-chlorophenyl)-4-cyano-5-aminopyrazole.

These compounds can be used as intermediates to prepare pyrazolo-triazolo-pyrimidine compounds as described herein.

Example 6

Preparation of 1-substituted-4-cyano-3-aminopyrazoles

Starting from 4-cyano-5-aminopyrazole, prepared according the procedure reported in *Chem. Pharm. Bull.* 1970, 18, 2353 or in *J. Heterocyclic Chem.* 1979, 16, 1113, 1-substituted 4-cyano-3-aminopyrazoles can be prepared by direct alkylation with the corresponding alkyl halide in dimethyl formamide at 80° C. for 1 to 2 h in the presence of anhydrous potassium carbonate. From the reaction mixture, containing the two N1 and N2 alkylated position isomers in an about 1:2 ratio, the N2 isomer can be isolated by a single crystallization or column chromatography on silica gel eluting with ethyl acetate and petroleum ether mixtures. Using these procedures, the following compounds were prepared:

1-methyl-4-cyano-3-aminopyrazole
1-butyl-4-cyano-3-aminopyrazole
1-benzyl-4-cyano-3-aminopyrazole
1-isopentyl-4-cyano-3-aminopyrazole
1-phenylethyl-4-cyano-3-aminopyrazole These compounds can be used as intermediates to prepare pyrazolo-triazolo-pyrimidine compounds as described herein.

Example 7

Preparation of phenylethyl-4-cyano-3-aminopyrazoles a) A suspension of anhydrous potassium carbonate (30 mmols) in DMF (50 ml) is added with 3-amino-4-cyano pyrazole (20 mmols), heating to a temperature of 80° C. for 30 minutes. The suspension is added with phenethyl bromide (25 mmols) and is heated to 80° C. for 2 h. After cooling to room temperature, the mixture is evaporated to dryness under vacuum and the resulting residue is taken up with distilled water (100 ml) and extracted with ethyl acetate (3×50 ml). The combined organic extracts are dried over anhydrous sodium sulfate and evaporated to dryness under vacuum. The resulting residue consists of a 1:3 mixture of 1-phenylethyl-4-cyano-5-aminopyrazole (20%) and of 1-phenylethyl-4-cyano-3-aminopyrazole (60%) which may be used as such in Example 9 or chromatographed on silica gel column eluting with an ethyl acetate/hexane mixture to give: 1-phenylethyl-4-cyano-5-aminopyrazole M.P. 172–173° C.; (20%); $^1H$-NMR (DMSO-d6): 3.04 (t, 2H); 4.12 (t, 2H); 5.85 (sb, 2H); 7.21–7.30 (m, 5H); 7.41 (s, 1H);

1-β-phenylethyl-4-cyano-3-aminopyrazole M.P. 98–100° C. (60%); $^1$H NMR (CDCl$_3$): 3.07 (t, 2H); 4.10 (t, 2H); 4.23 (sb, 2H); 7.17 (s, 1H); 7.00–7.28 (m, 5H).

b) A solution of 1-β-phenylethyl-4-cyano-5-aminopyrazole (20 mmol) in triethylorthoformate (40 ml) was refluxed under nitrogen for 8 h. The excess orthoformate was evaporated to dryness under vacuum and the residual yellow oil is dissolved in ethyl ether and percolated onto silica gel to give the corresponding iminoether (87% yield). The residue obtained after orthoformate evaporation is practically pure and is directly used in the following step. A solution of the iminoether (20 mmol) and 2-furoic acid hydrazide (2.5 g, 22 mmol) in 2-methoxyethanol (50 ml) was refluxed for 5 to 10 h. After cooling, the solution is evaporated to dryness to give an oily residue which is subjected to thermal cyclization in diphenylether (50 ml) using a Dean-Stark apparatus so as to azeotropically remove water formed during the reaction. After 1.5 h, the reaction is checked by TLC (ethyl acetate:petroleum ether 2:1) and when the starting compound is completely absent, the mixture is cooled and added with hexane. The resulting precipitate is filtered and crystallized to give 7-(β-phenylethyl)-2 (2-furyl)-pyrazolo[4,3-e]1,2,4-triazolo[1,5c]-pyrimidine M.P. 174–175° C. (20%) $^1$H NMR (DMSO-d 6): 3.23 (t, 2H) 4.74 (t, 2H); 6.75 (s, 1H); 7.14–7.17 (m, 5H); 7.28 (s, 1H); 7.98 (s, 1H); 8.53 (s, 1H); 9.56 (s, 1H).

In a similar way, starting from 1-β-phenylethyl-4-cyano-3-aminopyrazole, 8-(β-phenylethyl)-2(2-furyl) pyrazolo[4,3-e]1,2,4-triazole(1,5-c)-pyrimidine was prepared; M.P. 268–270° C. (600A) $^1$H NMR (DMSO-d6): 3.32 (t, 2H); 4.72 (t, 2H); 6.73 (s, 1H), 7.23 (m, 5H); 7.95 (s, 1H); 8.8 (s, 1H); 9.41 (s, 1H).

c) A suspension of the product of step b) (10 mmol) in 10% HCl (5.0 ml) is refluxed under stirring for 3 h. After cooling, the solution is alkalinized with concentrated ammonium hydroxide at 0° C. and the resulting precipitate is filtered or extracted with ethyl acetate (3×100 ml), dried and evaporated to dryness under vacuum, to give the corresponding 1-β-phenylethyl-4-[3(2-furyl)-1,2,4-triazol-5-yl]-5-amino pyrazole m.p. 175–176° C.; $^1$H NMR (DMSO-d6): 3.15 (t, 2H); 4.48 (t, 2H); 5.78 (s, 1H), 6.37 (s, 1H); 6.68 (s, 1H); 7.1 (s, 1H); 7.27–7.28 (m, 5H); 7.82 (s, 1H); 14.51 (bs, 2H): in a similar way 1-(β-phenylethyl)-4-[3(2-furyl)-1,2,4-triazol-5-yl)-3-aminopyrazole (m.p. 205–206° C.); $^1$H NMR (DMSO-d 6): 3.12 (t, 2H); 4.46 (t, 2H) 5.75 (s, 1H); 14.41 (bs, 2H) is obtained.

d) Cyanamide (60 mmol) is added to a suspension of the amine of step c) (10 mmol in N-methylpyrrolidone (40 ml) followed by p-toluene sulfonic acid (15 mmol). The mixture is heated to 160° C. under stirring. After 4 h a second portion of cyanamide (60 mmol) is added and heating is continued overnight. The mixture is then treated with hot water (200 ml) and the precipitate is filtered, washed with water and crystallized from ethanol to give the corresponding 5-amino-7-(β-phenylethyl)-2-(2-furyl)-pyrazolo[4,3-e]-1,2,4-triazole [1,5-c]pyrimidine m.p. 225–226° C. $^1$H NMR (DMSO-d 6): 3.21 (t, 2H); 4.51 (t, 2H); 6.65 (s, 1H); 7.1–7.44 (m, 6H); 7.78 (s, 1H); 7.89 (bs, 2H); 8.07 (s, 1H).

In a similar way 5-amino-8-(β-phenylethyl)-2-(2-furyl)-pyrazolo[4,3-e]-1,2,4-triazole[1,5c]-pyrimidine m.p. 212–213° C. $^1$H NMR (DMSO-d 6): 3.21 (t, 2H); 4.53 (t, 2H); 6.7 (s, 1H); 7.1–7.4 (m, 6H); 7.65 (sb, 2H); 7.93 (s, 1H); 8.45 (s, 1H) was obtained.

Example 8

Preparation of 4-cyano-5-amino-1,2,3-triazoles

A suspension of potassium carbonate (0.23 mole) in DMSO (70 ml) is added subsequently with cyanoacetamide (70 mmols) and p-fluorobenzylazide (54.5 mmols). The resulting solution is stirred at room temperature for 1 h and then poured into a large volume of water (1.5 l). The separated solid is filtered, washed with water and dried in oven at 70° C. to give 1-(p-fluorobenzyl)-4-carboxamido-5-amino-1,2,3-triazole (96.1% yield). M.P.: 198–199° C.; $^1$H NMR (DMSO-d 6): 7.5–7.1 (m, 6H); 6.4 (s, 2H); 5.4 (s, 2H). An amide suspension (0.005 mole), stirred and cooled to 0° C., in DMF (5 ml) is added with phosphorous oxychloride (0.01 mole). The resulting solution is stirred for 5 minutes at 0° C., 10 minutes at 25° C. and 15 minutes at 80° C. After cooling to room temperature, 5 ml of N HCl are added and the mixture is refluxed for 5 minutes. 1-(p-fluorobenzyl)-4-cyano-5-amino-1,2,3-triazole separates from the cooled solution (90% yield). M.P. 185–186° C.; $^1$H NMR (DMSO-d 6): 7.3–7.0 (m, 6H); 5.5 (s, 2H); IR (KBr): 3400, 3220, 2220, 1655 cm−1.

Analogously, the following compounds were prepared:

1- or 2-benzyl-4-cyano-5-amino-1,2,3-triazole 1- or 2-(o-fluorobenzyl)-4-cyano-5-amino-1,2,3-triazole
1- or 2-(p-fluorobenzyl)-4-cyano-5-amino-1,2,3-triazole 1- or 2-butyl-4-cyano-5-amino-1,2,3-triazole 1- or 2-isopentyl-4-cyano-5-amino-1,2,3-triazole 1- or 2-(2-methoxyethyl)-4-cyano-5-amino-1,2,3-triazole
1-2-heptyl-4-cyano-5-amino-1,2,3-triazole 1- or 2-octyl-4-cyano-5-amino-1,2,3-triazole.

These compounds can be used as intermediates to prepare the triazolo-triazolo-pyrimidine compounds as described herein.

Example 9

Preparation of Ethoxymethyleneamino Heterocycles

The preparation of ethoxymethyleneamino heterocycles of formula IV is performed refluxing the respective ortho-aminonitrile with ethyl orthoformate. By way of example, the preparation of 4-cyano-5-(ethoxymethyleneamino)-1-butylpyrazole is reported. A solution of 4-cyano-5-amino-1-butylpyrazole (20 mmols) in triethyl orthoformate (40 ml) is heated to the reflux temperature under nitrogen atmosphere for 8 h. The orthoformate excess is evaporated to dryness under vacuum and the residual yellow oil is dissolved in ethyl ether and eluted through silica gel to give the pure compound (87% yield). In many cases, the residue obtained after evaporation of the orthoformate is substantially pure and is used as such in the subsequent step. IR (nujol): 3140, 2240, 1640 cm−1; $^1$H NMR (CDCl$_3$): 8.4 (s, 1H); 7.9 (s, 2H); 4.5 (t, 2H); 4.3 (q, 2H); 1.8 (m, 2H); 1.5 (m, 2H); 1.4 (t, 3H); 0.9 (t, M).

Example 10

Cyclization of Ethoxymethyleneamino Heterocycles

A solution of the ethoxymethyleneamino heterocycle (20 mmols) and 2-furoic acid hydrazide (2.5 g, 22 mmol) in 2-methoxyethanol (50 ml) is refluxed for 5 to 10 h. After cooling, the solution is evaporated to dryness to obtain a residual oil which is subjected to thermal cyclization in diphenyl ether (50 ml) using a round-bottom flask fitted with a Dean-Stark apparatus, to azeotropically remove the water formed during the reaction. After varying times (3 to 5 h) the reaction is checked by TLC (2:1 ethyl acetate: petroleum ether) and when the whole starting product has disappeared, the mixture is cooled and hexane is added. The resulting precipitate is filtered and crystallized from the suitable solvent. In some cases, a viscous oil separates from the solution, which is then decanted and subsequently extracted. The oily residue is then chromatographed on silica gel, eluting with ethyl acetate/petroleum ether mixtures, to give the tricyclic compound VI.

By way of examples, the analytical and spectroscopical characteristics of some compounds prepared by these procedures are reported:

7-butyl-2(2-furyl)-pyrazolo-[4,3-e]1,2,4-triazolo[1,5-c]pyrimidine. $^1$H NMR (DMSO-d 6): 9.6 (s, 1H); 8.6 (s, 1H); 8.0 (m, 1H); 7.4 (m, 1H); 6.7 (m, 1H); 4.5 (t, 2H); 1.9 (m, 2H); 1.3 (m, 2H); 0.9 (t, 3H).

8-butyl-2(2-furyl)-pyrazolo[4,3-e]1,2,4-triazolo[1,5-c]pyrimidine. $^1$H NMR (DMSO-d 6): 9.4 (s, 1H); 8.9 (s, 1H); 8.0 (m, 1H), 7.3 (m, 1H); 6.2 (m, 1H); 4.5 (t, 2H); 1.9 (m, 2H); 1.; (m, 2H); 0.9 (m, 3H). In the 2D-NMR (NOESY) spectrum, the N—CH$_2$ signal resonating at 4.5 shows cross peaks with the C9-H signal resonating at 8.9.

7-isopentyl-2(2-furyl)-pyrazolo[4,3-e]1,2,4-triazolo[1,5-c]pyrimidine. $^1$H NMR (CDCl$_3$): 9.1 (s, 1H); 8.8 (s, 1H); 7.7 (m, 1H); 7.3 (m, 1H); 6.6 (m, 1H); 4.6 (t, 2H); 1.18–1.7 (m, 3H); 1.0 (d, 6H).

8-isopentyl-2(2-furyl)-pyrazolo[4,3-e]1,2,4-triazolo[1,5-c]pyrimidine. 9.1 (s, 1H); 8.8 (s, 1H); 7.7 (m, 1H); 7.3 (m, 1H); 6.6 (m, 1H); 4.6 (t, 2H); 1.9–1.5 (m, 3H); 1.0 (d, 6H).

Following this procedure, the following compounds were prepared:

7-methyl-2(2-furyl)-pyrazolo[4,3-e]1,2,4-triazolo[1,5-c]pyrimidine 8-methyl-2(2-furyl)-pyrazolo[4,3-e]1,2,4-triazolo[1,5-c]pyrimidine 7-(2-chlorophenyl)-2(2-furyl)-pyrazolo[4,3-e]1,2,4triazolo[1,5-c]pyrimidine 7-phenylethyl-2(2-furyl)-pyrazolo[4,3-e]1,2,4-triazolo[1,5-c]pyrimidine 7-tert-butyl-2(2-furyl)-pyrazolo[4,3-e]1,2,4-triazolo[1,5-c]pyrimidine 7-(2-cyclopentyl)ethyl-2(2-furyl)-pyrazolo[4,3-e]1,2,4 triazolo(1,5-c)pyrimidine 8-benzyl-2(2-furyl)-pyrazolo[4,3-e]1,2,4-triazolo[1,5-c]pyrimidine 7-benzyl-2(2-furyl)-1,2,3-triazolo[5,4-e]1,2,4-triazolo[1,5-c]pyrimidine 7-(2-fluorobenzyl)-2(2-furyl)-1,2,3-triazolo[5,4-e]1,2,4-triazolo[1,5-c]pyrimidine 7-(4-fluorobenzyl)-2(2-furyl)-1,2,3-triazolo[5,4e]1,2,4-triazolo[1,5-c]pyrimidine 7-butyl-2(2-furyl)-1,2,3-triazolo[5,4-e]1,2,4-triazolo[1,5-c]pyrimidine 7-isopentyl-2(2-furyl)-1,2,3-triazolo[5,4-e]1,2,4-triazolo[1,5-c]pyrimidine 7-(2-methoxy)ethyl-2-(2-furyl)-1,2,3-triazolo[5,4-e]-1,2,4-triazolo[1,5-c]pyrimidine 7-heptyl-2-(2-furyl)-1,2,3-triazolo[5,4-e]-1,2,4-triazolo[1,5-c]pyrimidine 7-octyl-2-(2-furyl)-1,2,3-triazolo[5,4-e]1,2,4-triazolo[1,5-c]pyrimidine 8-benzyl-2(2-furyl)-1,2,3-triazolo[5,4-e]1,2,4-triazolo[1,5-c]pyrimidine 8-(2-fluorobenzyl)-2-(2-furyl)-1,2,3-triazolo[5,4-e]1,2,4-triazolo[1,5-c]pyrimidine 8-(4-fluorobenzyl)-2-(2-furyl)-1,2,3-triazolo[5,4-e]1,2,4-triazolo[1,5-c]pyrimidine 8-butyl-2-(2-furyl)-1,2,3-triazolo[5,4-e]1,2,4-triazolo[1,5-c]pyrimidine 8-isopentyl-2-(2-furyl)-1,2,3-triazolo[5,4-e]1,2,4-triazolo[1,5-c]pyrimidine 8-hexyl-2-(2-furyl)-1,2,3-triazolo[5,4-e]1,2,4-triazolo[1,5-c]pyrimidine 8-heptyl-2-(2-furyl)-1,2,3-triazolo[5,4-e]1,2,4-triazolo[1,5-c]pyrimidine 8-octyl-2-(2-furyl)-1,2,3-triazolo[5,4-e]1,2,4-triazolo[1,5-c]pyrimidine 9-benzyl-2-(2-furyl)-1,2,3-triazolo[4,5-e]1,2,4-triazolo[1,5-c]pyrimidine 9-(2-fluorobenzyl)-2-(2-furyl)-1,2,3-triazolo[4,5-e]1,2,4-triazolo[1,5-c]pyrimidine 9-(4-fluorobenzyl)-2-(2-furyl)-1,2,3-triazolo[4,5-e]1,2,4-triazolo[1,5-c]pyrimidine These compounds can be used as intermediates to prepare the triazolo-triazolo-pyrimidines and pyrazolo-triazolo-pyrimidines as described herein.

Example 11

Preparation of 5-amino-7-[aralkyl)]-2-(2-furyl)-pyrazole[4,3-e]-1,2,4-triazole[1,5-c]pyrimidines A suspension of the amines of formula VII (10 mmols) in N-methylpyrrolidone (40 ml) is added with cyanamide (60 mmols) followed by p-toluenesulfonic acid (15 mmols). The mixture is heated to 160° C. with magnetic stirring. After 4 h, a second portion of cyanamide (60 mmols) is added and heating is continued overnight. The mixture is then treated with hot water (200 ml) and the precipitated solid is filtered, washed with water and crystallized from ethanol. If no precipitations take place, the solution is extracted with ethyl acetate (4×100 ml), the extracts are washed with brine (2×50 ml), dried and evaporated to dryness under vacuum. The residue is then chromatographed on a silica gel column eluting with ethyl acetate. In the following, the analytical and spectroscopic data of some compounds prepared by this procedure are reported:

5-amino-7-butyl-2-(2-furyl)-pyrazolo[4,3-e]-1,2,4-triazolo[1,5-c]pyrimidine. M.P. 157–158° C.; $^1$H NMR (DMSO-d 6) 8.1 (s, 1H); 8.0 (s, 2H); 7.9 (m, 1H); 7.2 (m, 1H); 6.7 (m, 1H); 4.2 (t, 2H); 1.9 (m, 2H); 1.5 (m, 2H); 0.9 (t, 3H). 5-amino-8-butyl-2-(2-furyl)-pyrazolo[4,3-e]-1,2,4-triazolo[1,5-c]pyrimidine m.p. 183–185° C.; $^1$H NMR (DMSO-d 6): 8.6 (s, 1H); 8.0 (s, 1H); 7.6 (s, 2H); 7.2 (m, 1H); 6.7 (m, 1H); 4.2 (t, 2H); 1.8 (m, 2H); 1.2 (m, 2H); 0.9 (t, 3H).

5-amino-7-benzyl-2-(2-furyl)-1,2,3-triazolo[5,4-e]1,2,4-triazolo[1,5-c]pyrimidine. M.p. 295–297° C.; $^1$H NMR (DMSO-d 6): 8.5 (s, 2H); 8.0 (s, 1H); 7.3 (m, 6H); 6.7 (m, 1H); 5.7 (s, 2H).

5-amino-7-o-fluoro-benzyl-2-(2-furyl)-1,2,3-triazolo[5,4-e]-1,2,4-triazolo[1,5-c]pyrimidine M.p. 310–312° C.; $^1$H NMR (DMSO-d 6): 8.5 (s, 2H); 8.0 (s, 1H); 7.3 (m, 5H); 6.8 (s, 1H); 5.75 (s, 2H).

5-amino-7-methyl-2-(2-furyl)-pyrazolo[4,3-e]-1,2,4triazolo-[1,5-c]pyrimidine; m.p. 210–213° C.

5-amino-7-tert-butyl-2-(2-furyl)-pyrazolo[4,3-e]-1,2,4triazolo-[1,5-c]pyrimidine; m.p. 238–240° C.

5-amino-2-(2-furyl)-pyrazolo[4,3-e]-1,2,4-triazolo (1,5-c)pyrimidine; m.p. 248–250° C.

5-amino-7-(2-hydroxyethyl)-2-(2-furyl)-pyrazolo[4,3-e]1,2,4-triazolo-[1,5-c]pyrimidine; m.p. 258–260° C.

5-amino-7-phenyl-2-(2-furyl)-pyrazolo(4,3-e]-1,2,4triazolo-[1,5-c]pyrimidine; m.p. 295–297° C.

5-amino-7-isopentyl-2-(2-furyl)-pyrazolo[4,3-e]-1,2,4triazolo-[1,5-e]pyrimidine; m.p. 208–210° C.

5-amino-8-isopentyl-2-(2-furyl)-pyrazolo(4,3-e)-1,2,4triazolo- 1,5-c]pyrimidine;. m.p. 200–203° C.

5-amino-7-phenethyl-2-(2-furyl)-pyrazolo[4,3-e]-1,2,4-triazolo-[1,5-c]pyrimidine; m.p. 225° C.

5-amino-7-benzyloxyethyl-2-(2-furyl)-pyrazolo[4,3-e]1,2,4-triazolo-[1,5-c]pyrimidine.

5-amino-7-[β-(4-isobutylphenethyl)]-2-(2-furyl)-pyrazole[4,3-e]-1,2,4-triazole[1,5-c]pyrimidine m.p. 207–210° C.

These compounds can be reacted with a suitable acid or sulfonic acid derivative to arrive at the compounds of Formula I disclosed herein.

Example 12

Preparation of Substituted-4-carboxamido-5-amino-1,2,3-triazoles p-Fluorobenzylazide (15.1 g, 0.1 mole) and cyanacetamide (10.8 g, 0.13 moles) are added in this order to a suspension of powdered potassium carbonate (57.5 g, 0.42 mole) in dimethylsulfoxide (150 ml). The mixture is stirred at room temperature, for 1 h. The mixture is poured into 3 liters of water and the solid which separates is filtered and washed thoroughly with water to give 22.47 g (96%) of 1-p-fluorobenzyl-4-carboxamido-5-amino 1,2,3-triazole. M.P.: 198–199° C.; $^1$H NMR (DMSO-d 6): 7.5–7.1 (m, 6H); 6.4 (s, 2H); 5.4 (s, 2H).

Analogously, 2-fluoro-6-chlorobenzyl-4-carboxamide-5-amino-1,2,3-triazole; m.p. 230–231° C.; $^1$H NMR (DMSO d 6): 5.40 (s, 2H); 6.52 (bs, 2H); 7.12–7.45 (m, 5H).

3-fluorobenzyl-4-carboxamido-5-amino 1,2,3-triazole; m.p. 211–211° C. $^1$H-NMR (DMSO d 6): 5.46 (s, 2H); 6.47 (bs, 2H); 7.00–7.52 (m, 6H).

2-fluorobenzyl-4-carboxamido-5-amino-1,2,3-triazole; M.P. 195–197° C.

1-(β-phenylethyl)-4-carboxamido-5-amino-1,2,3-triazole; M.P. 181–183° C.; $^1$H NMR (DMSO-d6): 3.04 (t, 2H); 4.35 (t, 2H); 6.30 (sb, 2H); 7.20–7.47 (m, 7H) are obtained.

Example 13

Preparation of Substituted-4-cyano-5-amino-1,2,3-triazoles

A suspension of 1-p-fluorobenzyl-4-carboxamido-5amino-1,2,3-triazole (23.4 g, 0.1 mole) in DMF (100 10 ml), magnetically stirred at 0° C., is added with 20.8 ml (0.2 mole) of POCl$_3$. The solution is stirred for 5 h at 0° C., 10 h at room temperature and finally 15 h at 80° C. After cooling, 1N HCl (100 ml) is added thereto and the resulting solution is refluxed for 5 h; upon cooling 1,5 p-fluorobenzyl-4-cyano-5-amino-1,2,3-triazole (18.54 g, 90%) precipitates. M.P. 185–186° C.; $^1$H NMR (DMSO-d6): 7.3–7.0 (m, 6H); 5.5 (s, 2H); IR (KBr): 3400, 3220, 2220, 1655 cm–1.

Analogously, the following compounds are obtained:

2-fluoro-6-chlorobenzyl-4-cyano-5-amino-1,2,3-triazole; M.P. 181–185° C. $^1$H NMR (DMSO-d 6): 5.40 (s, 2H); 7.26–7.50 (m, 5H).

3-fluorobenzyl-4-cyano-5-amino-1,2,3-triazole; M.P. 195–197° C. $^1$H NMR (DMSO d 6): 5.44 (s, 2H); 7.00–7.43 (m, 6H).

2-fluorobenzyl-4-cyano-5-amino-1,2,3-triazole; M.P.: 195–197° C.

1-(β-phenylethyl)-4-cyano-5-amino-1,2,3-triazole; M.P. 149–150° C. $^1$H NMR (DMSO-d 6): 3.04 (t, 2H), 4.36 (t, 2H); 7.03 (sb, 2H); 7.23–7.28 (m, 5H).

Example 14

Preparation of Substituted-4[3(2-furyl)-1,2,4-triazol-5-yl]-5-amino-1,2,3-triazoles A suspension of 1-p-fluorobenzyl-4-cyano-5-amino-1,2,3-triazole (20 mmols) and 2-furoic acid hydrazide (22 mmols) in diphenyl ether (30 ml) is stirred and heated to reflux (260° C.) with a Dean-Stark apparatus until the starting compound disappears (TLC, 1 to 2 h). After cooling, the mixture is diluted with petroleum ether and the resulting precipitate is either filtered or separated by decantation and chromatographed on a silica gel column eluting with 2:1 ethyl acetate and petroleum ether.

1-p-fluorobenzyl-4[3-(2-furyl)-1,2,4-triazol-5-yl]-5-amino-1,2,3-triazole; m.p. 266–268° C. $^1$H NMR (DMSO-d 6): 14.5 (s, 1H); 7.8 (s, 1H); 7.4–7.1 (m, 5H); 6.6 (s, 1H); 6.5 (s, 2H); 5.5 (s, 2H).

Analogously, 1-(β-phenylethyl)-4[3(2-furyl)-1,2,4-triazol-5-yl]-5-amino1,2,3-triazole (50%); m.p. 200–202° C. $^1$H-NMR (DMSO-d6): 3.07 (t, 2H); 4.16 (t, 2H); 5.50 (sb, 2H); 6.61 (s, 1H); 6.95 (s, 1H); 7.2–7.4 (m, 5H); 7.78 (s, 1H); 13.8 (bs, 1H) is obtained.

Example 15

Preparation of 5-amino-7-Substituted-2-(2-furyl)-1,2,3-triazolo[5,4-e]1,2,4-triazolo[1,5-c]pyrimidines A suspension of 1-p-fluorobenzyl-4[3-(2-furyl)1,2,4-triazol-5-yl]-5-amino-1,2,3-triazole (0.325 g, 1 mmols) in N-methyl-pyrrolidone (4 ml) is added with cyanamide (6 mmols) followed by p-toluenesulfonic acid (1.5 mmols). The mixture is heated at 160° C. with magnetic stirring. After 4 h, a second portion of cyanamide (6 mmols) is added and heating is continued overnight. The mixture is then treated with hot water (20 ml) and the precipitated solid is filtered, washed with water and crystallized from ethanol. If no precipitations take place, the solution is extracted with ethyl acetate (4×10 ml), the extracts are washed with brine (2×5 ml), dried and evaporated to dryness under vacuum. The residue is then chromatographed on a silica gel column eluting with ethyl acetate to give 105 mg (30% yield) of 5-amino-7-p-fluoro-benzyl-2-(2-furyl)-1,2,3-triazolo[5,4-e]1,2,4-triazolo[1,5-c]pyrimidine M.P.: 266–268° C.; $^1$H NMR (DMSO-d 6): 8.5 (sb, 2H); 7.95 (s, 1H); 7.4–7.1 (m, 6H); 6.7 (s, 1H); 5.7 (s, 2H).

Analogously, were obtained:

5-amino-7-o-fluorobenzyl-2-(2-furyl)-1,2,3-triazolo[5,4-e]1,2,4-triazolo[1,5-c]pyrimidine; M.P. 310° C.

5-amino-7-benzyl-2-(2-furyl)-1,2,3-triazolo[5,4-e]1,2,4-triazolo[1,5-c]pyrimidine; M.P. 295–297° C.

5-amino-7-(2-fluoro-6-chlorobenzyl)-2-(2-furyl)-1,2,3-triazolo-5,4-e]1,2,4-triazolo[1,5-c]pyrimidine; M.P. 218–220° C.; $^1$H NMR (DMSO-d6): 8.51 (sb', 2H); 7.98 (s, 1H); 7.55–7.28 (m, 4H); 6.77 (m, 1H); 5.73 (s, 2H).

5-amino-7-(m-fluorobenzyl)-2-(2-furyl) 1,2,3triazolo[5,4-e]1,2,4-triazolo[1,5-c]pyrimidine; m.p. 280–283° C.; $^1$H NMR (DMSO-d6): 8.45 (bs, 2H); 7.98 (s, 1H); 7.4–7.1 (m, 5H); 6.76 (s, 1H); 5.75 (s, 2H).

5-amino-7-(β-phenylethyl)-2-(2-furyl)-1,2,3 triazolo[5,4-e]1,2,4-triazolo[1,5-c]pyrimidine; M.P. 269–271° C.; $^1$H NMR (DMSO-d6): 8.4 (sb, 2H); 7.98 (s, 1H); 7.3–7.15 (m, 6H); 6.8 (s, 1H); 4.71 (t, 2H); 3.31 (t, 2H) are obtained.

Example 16

Evaluation of the Biological Activity of the Compounds

Several of the compounds described above have been tested for their affinity at rat $A_1$ and $A_{2A}$ and human $A_3$ receptors using the following assays.

Rat $A_1$ and $A_{2A}$ Adenosine Receptor Binding Assay

Male Wistar rats (200–250 g) were decapitated and the whole brain and striatum dissected on ice. The tissues were disrupted in a polytron homogenizer at a setting of 5 for 30 s in 25 volumes of 50 mM Tris HCl, pH 7.4, containing 10 mM $MgCl_2$. The homogenate was centrifuged at 48,000 for 10 min, and the pellet was resuspended in the same buffer containing 2 IU/mL adenosine deaminase. After 30 min incubation at 37° C., the membranes were centrifuged and pellets were stored at –80° C. Prior to freezing, an aliquot of homogenate was removed for protein assay with bovine albumin as reference standard. Binding assays were performed on rat brain and striatum membranes respectively, in the presence of 10 mM $MgCl_2$ at 25° C. All buffer solutions were adjusted to maintain a constant pH of 7.4.

Displacement experiments were performed in 500 μL of Tris HCl buffer containing 1 nM of the selective adenosine $A_1$ receptor ligand [$^3$H]CHA ($N^6$-cyclohexyladenosine) and membranes of rat brain (150–200 μg- of protein/assay).

Displacement experiments were performed in 500 μL of Tris HCl buffer containing 10 mM $MgCl_2$, 0.2 nM of the selective adenosine $A_{2A}$ receptor ligand [$^3$H]SCH58261 (5-amino-7-(2-phenylethyl)-2(2-furyl)-pyrazolo[4,3-e]-1,2,4-triazolo[1,5-c]pyrimidine) and membranes of rat striatum (80–100 μg of protein/assay). To determine $IC_{50}$ values (where $IC_{50}$ is the inhibitor concentration displacing 50% of labeled ligand) the test compound was added in triplicate to binding assay samples at a minimum of six different concentrations. Separation of bound from free radio ligand was performed by rapid filtration through Whatman GF/B filters which were washed three times with ice-cold buffer. Filter bound radioactivity was measured by scintillation spectrometry after addition of 5 mL of Aquassure. Non specific binding was defined as binding in the presence of 10 μM R-PIA ($N^6$-(phenylisopropyl)adenosine) and 10 μM NECA (5'-(N-ethylcarboxamido) adenosine), respectively, and was always 10% of the total binding. Incubation time ranged from 150 min. at 0° C. to 75 min at 30° C. according to the results of previous time-course experiments. Ki values were calculated from the Cheng-Prusoff equation. All binding data were analyzed using the nonlinear regression curve-fitting computer program LIGAND.

Human Cloned $A_3$ Adenosine Receptor Binding Assays.

An aliquot of membranes (8 mu of protein/mL) from HEK-293 cells transfected with the human recombinant $A_3$ adenosine receptor was used for binding assays. FIG. 1 shows a typical saturation of [$^{125}$I]AB-MECA ($N^6$-(4-amino-3-iodobenzyl)-5'-(N-methylcarbamoyl)adenosine) to HEK-293 cells. Inhibition experiments were carried out in duplicate in a final volume of 100 μL in test tub containing 0.3 nM [$^{125}$I]AB-MECA, 50 nM Tris HCL buffer, 10 mM $MgCl_2$, pH 7.4, 20 μL of diluted membranes (12.4 mg of protein/mL), and at least 6–8 different concentrations of typical adenosine receptor antagonists. Non-specific binding was defined in the presence of 50 μM R-PIA and was about 30% of total binding. Incubation time was 60 min at 37° C., according to the results of previous time-course experiments. Bound and free radioactivity was separated by filtering the assay mixture through Whatman GF/B glass-fiber filters using a Brandel cell harvester.

Results and Discussion

Compounds 38, 40, 41, 50, 51, and 54–57 were tested in radio ligand binding assays for affinity at rat brain $A_1$, $A_{2A}$ and human $A_3$ receptors, and the results are summarized in Table 1.

The data demonstrate that compounds lacking bulky (compounds 38, 40 and 41) groups at $N^5$ position show great affinity for $A_{2A}$ adenosine receptors with low selectivity vs. $A_1$ and low affinity at human adenosine $A_3$ receptor subtype, and that compounds with substituted phenyl carbamoyl chain at $N_5$ position possess affinity in nanomolar range at $hA_3$ receptor subtype with different degree of selectivity vs. $A_1$ and $A_{2A}$ receptor subtype. In particular, the 4-methoxyphenylcarbamoyl moiety (compounds 51, 55 and 57) confers higher affinity, of about three order of magnitude, than 3-chlorophenylcarbamoyl residue (compounds 50, 54 and 56).

Derivatives with a β-phenylethyl chain at $N^8$ and 4-MeO-phenylcarbamoyl chain at $N^5$ positions (compound 55) showed the best values in terms of affinity and selectivity. ($K_ihA_3$=1.47 nM, $rA_1/hA_3$ =872, $rA_{2A}/hA_3$=951).

The introduction, at the $N^8$ position, of chains with different steric characteristics permits the design of derivatives with high potency at human $A_3$ adenosine receptor and better selectivity vs. $A_1$ and $A_{2A}$ receptor subtypes.

FIG. 1 shows a saturation curve of [$^{125}$I]AB-MECA to adenosine $A_3$ receptor and the linearity of the Scatchard plot in the inset is indicative, in our experimental conditions, of the presence of a single class of binding sites with $K_D$ value of 0.9±0.01 nM and Bmax value of 62±1 fmol/mg protein (n=3).

TABLE 1

Binding affinity at $rA_1$, $rA_{2A}$ and $hA_3$ adenosine receptors of compounds 38, 40, 41, 50, 51, and 54–57

| Compound | $R^2$ | R | $rA_1$ ($K_i$, nM) | $rA_{2A}$ ($K_i$, nM) | $hA_3$ ($K_i$, nM) | $rA_1/hA_3$ | $rA_{2A}/hA_3$ |
|---|---|---|---|---|---|---|---|
| 38 | $(CH_3)_2CH—CH_2—CH_2$ | H | 8.09 (7.46–8.78) | 1.20 (1.03–1.40) | 1,163 (1,024–1,320) | 0.007 | 0.001 |
| 51 | $(CH_3)_2CH—CH_2—CH_2—$ | 4-MeO—Ph—NHCO | 476 (432–525) | 376 (332–426) | 29.57 (26.94–32.46) | 16 | 13 |
| 50 | $(CH_3)_2CH—CH_2—CH_2$ | 3-Cl—Ph—NHCO | 1,650 (1,560–1,744) | 1,197 (1,027–1,396) | 81.10 (68.45–96.09) | 20 | 15 |

TABLE 1-continued

Binding affinity at rA₁, rA₂ₐ and hA₃ adenosine receptors of compounds 38, 40, 41, 50, 51, and 54–57

| Compound | R² | R | rA₁ ($K_i$, nM) | rA₂ₐ ($K_i$, nM) | hA₃ ($K_i$, nM) | rA₁/hA₃ | rA₂ₐ/hA₃ |
|---|---|---|---|---|---|---|---|
| 40 | Ph—CH₂—CH₂ | H | 2.16 (1.9–2.47) | 0.70 (0.53–0.91) | 2,785 (2,463–3,149) | 0.0007 | 0.0002 |
| 55 | Ph—CH₂—CH₂ | 4-MeO—Ph—NHCO | 1,282 (1,148–1,432) | 1,398 (1,225–1,594) | 1.47 (1.22–1.78) | 872 | 951 |
| 54 | Ph—CH₂—CH₂ | 3-Cl—Ph—NHCO | 1,049 (961–1,145) | 1,698 (1,524–1,892) | 13.28 (10.87–16.23) | 79 | 128 |
| 41 | Ph—CH₂—CH₂—CH₂ | H | 11.13 (9.34–13.27) | 0.59 (0.44–0.81) | 2,666 (2,533–2,805) | 0.004 | 0.0002 |
| 57 | Ph—CH₂—CH₂—CH₂ | 4-MeO—Ph—NHCO | 1,514 (1,332–1,721) | >10,000 | 19.81 (17.61–22.27) | 76.4 | >504 |
| 56 | Ph—CH₂—CH₂—CH₂ | 3-Cl—Ph—NHCO | >10,000 | 3,200 (3,025–3,385) | 42.65 (39.92–45.57) | >234 | 75 |

Example 17

Pharmaceutical Formulations (A) Transdermal System-for 1000 patches

| Ingredients | Amount |
|---|---|
| Active compound | 100 g |
| Silicone fluid | 450 g |
| Colloidal silicon dioxide | 2 g |

(B) Oral Tablet-For 1000 Tablets

| Ingredients | Amount |
|---|---|
| Active compound | 50 g |
| Starch | 50 g |
| Magnesium Stearate | 5 g |

The active compound and the starch are granulated with water and dried. Magnesium stearate is added to the dried granules and the mixture is thoroughly blended. The blended mixture is compressed into tablets.

(c) Injection-for 1000, 1 mL Ampules

| Ingredients | Amount |
|---|---|
| Active compound | 10 g |
| Buffering Agents | q.s. |
| Propylene glycol | 400 mg |
| Water for injection | q.s. 1000 mL |

The active compound and buffering agents are dissolved in the propylene glycol at about 50° C. The water for injection is then added with stirring and the resulting solution is filtered, filled into ampules, sealed and sterilized by autoclaving.

(D) Continuous Injection-for 1000 mL

| Ingredients | Amount |
|---|---|
| Active compound | 10 g |
| Buffering agents | q.s. |
| Water for injection | q.s. 1000 mL |

Those skilled in the art will recognize, or be able to ascertain using no more than routine experimentation, many equivalents to the specific embodiments of the invention described herein. Such equivalents are intended to be encompassed by the following claims.

What is claimed is:

1. A compound of the following formula:

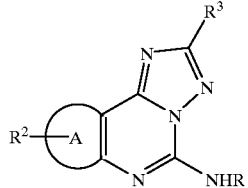

wherein:

A is imidazole, pyrazole, or triazole;

R is —C(X)R¹, —C(X)—N(R¹)₂, —C(X)OR¹, —C(X) SR¹, —SO$_n$—R¹, —SO$_n$OR¹, —SO$_n$—SR¹, or SO$_n$— N(R¹)₂;

R¹ is hydrogen, alkyl, substituted alkyl, alkenyl, substituted alkenyl, alkynyl, substituted alkynyl, aryl, heteroaryl, heterocyclic, lower alkenyl, lower alkanoyl, or, if linked to a nitrogen atom, then taken together with the nitrogen atom, forms an azetidine ring or a 5–6 membered heterocyclic ring containing one or more heteroatoms;

R² is hydrogen, alkyl, substituted alkyl, aralkyl, substituted aralkyl, heteroaryl, substituted heteroaryl or aryl;

R³ is furan, pyrrole, thiophene, benzofuran, benzopyrrole, benzothiophene, optionally substituted with one or more substituents selected from the group consisting of hydroxy, acyl, alkyl, alkoxy, alkenyl, alkynyl, substituted alkyl, substituted alkoxy, substituted alkenyl, substituted alkynyl, amino, substituted amino, aminoacyl, acyloxy, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and trihalomethyl;

X is O, S, or NR$^1$;

n is 1 or 2; and pharmaceutically acceptable salts thereof.

2. The compound of claim 1 wherein R is —C(X)R$^1$, —C(X)—N(R$^1$)$_2$, —SO$_n$R$^1$ or —SO$_n$—N(R$^1$)$_2$ wherein X is O or S.

3. The compound of claim 1 wherein R$^1$ is selected from the group consisting of hydrogen, alkyl, alkenyl and aryl.

4. The compound of claim 1 wherein R$^2$ is selected from the group consisting of hydrogen, alkyl and aryl.

5. The compound of claim 1 wherein R$^3$ is furan.

6. The compound of claim 1 wherein X is O.

7. The compound of claim 1 wherein A is a triazolo ring.

8. The compound of claim 1 wherein A is a pyrazolo ring.

9. A method of treating hypertension, inflammation, allergic reactions, mast cell degranulation, and cardiac hypoxia, and protecting against cerebral ischemia, comprising administering to a patient in need of treatment thereof an effective amount of a compound of claim 1.

10. The method of claim 9 wherein R is —C(X)R$^1$, —C(X)—N(R$^1$)$_2$, —SO$_n$R$^1$ or —SO$_n$—N(R$^1$)$_2$ wherein X is O or S.

11. The method of claim 9 wherein R$^1$ is selected from the group consisting of hydrogen, alkyl, alkenyl and aryl.

12. The method of claim 9 wherein R$^2$ is selected from the group consisting of hydrogen, alkyl and aryl.

13. The method of claim 9 wherein X is O.

14. The method of claim 9 wherein A is a pyrazolo ring.

15. The method of claim 9 wherein A is a triazolo ring.

16. The method of claim 9 wherein the disorder to be treated is selected from the group consisting of cardiac hypoxia and cerebral ischemia.

17. A compound selected from the group of compounds consisting of:

5-[[(3-Chlorophenyl)amino]carbonyl]amino-8-methyl-2-(2-furyl)-pyrazolo[4,3-e]-1,2,4-triazolo[1,5-c]pyrimidine, 5-[[(4-Methoxyphenyl)amino]carbonyl]amino-8-methyl-2-(2-furyl)-pyrazolo[4,3-e]-1,2,4-triazolo[1,5-c]pyrimidine, 5-[[(3-Chlorophenyl)amino]carbonyl]amino-8-ethyl-2-(2-furyl)-pyrazolo[4,3-e]-1,2,4-triazolo[1,5-c]pyrimidine, 5-[[(4-Methoxyphenyl)amino]carbonyl]amino-8-ethyl-2-(2-furyl)-pyrazolo[4,3-e]-1,2,4-triazolo[1,5-c]pyrimidine, 5-[[(3-Chlorophenyl)amino]carbonyl]amino-8-propyl-2-(2-furyl)-pyrazolo[4,3-e]-1,2,4-triazolo[1,5-c]pyrimidine, 5-[[(4-Methoxyphenyl)amino]carbonyl]amino-8-propyl-2-(2-furyl)-pyrazolo[4,3-e]-1,2,4-triazolo[1,5-c]pyrimidine, 5-[[(3-Chlorophenyl)amino]carbonyl]amino-8-butyl-2-(2-furyl)-pyrazolo[4,3-e]-1,2,4-triazolo[1,5-c]pyrimidine, 5-[[(4-Methoxyphenyl)amino]carbonyl]amino-8-butyl-2-(2-furyl)-pyrazolo[4,3-e]-1,2,4-triazolo[1,5-c]pyrimidine, 5-[[(3-Chlorophenyl)amino]carbonyl]amino-8-isopentyl-2-(2-furyl)-pyrazolo[4,3-e]-1,2,4-triazolo[1,5-c]pyrimidine, 5-[[(4-Methoxyphenyl)amino]carbonyl]amino-8-isopentyl-2-(2-furyl)-pyrazolo[4,3-e]-1,2,4-triazolo[1,5-c]pyrimidine, 5-[[(3-Chlorophenyl)amino]]carbonyl]amino-8-(2-isopentenyl)-2-(2-furyl)pyrazolo[4,3-e]1,2,4-triazolo[1,5-c]pyrimidine, 5-[[(4-Methoxyphenyl)amino]carbonyl]amino-8-(2-isopentenyl)-2-(2-furyl)-pyrazolo[4,3-e]-1,2,4-triazolo[1,5-c]pyrimidine, 5-[[(3-Chlorophenyl)amino]carbonyl]amino-8-(2-phenylethyl)-2 (2-furyl)-pyrazolo[4,3-e]-1,2,4-triazolo[1,5-c]pyrimidine, 5-[[(4-Methoxyphenyl)amino]carbonylamino-8-(2-phenylethyl)-2-(2-furyl)-pyrazolo[4,3-e]-1,2,4-triazolo[1,5-c]pyrimidine, 5-[[(3-Chlorophenyl)amino]carbonyl]amino-8-(3-phenylpropyl)-2-(2-furyl)-pyrazolo[4,3-e]-1,2,4-triazolo[1,5-c]pyrimidine, 5-[[(4-Methoxyphenyl)amino]carbonyl]amino-8-(3-phenylpropyl)-2-(2-furyl)-pyrazolo[4,3-e]-1,2,4-triazolo[1,5-c]pyrimidine, 5-[(Benzyl)carbony]amino-8-isopentyl-2-(2-furyl)-pyrazolo[4,3-e]-1,2,4-triazolo[1,5-c]pyrimidine, and 5-[(Benzyl)carbonyl]amino-8-(3-phenylpropyl)-2-(2-furyl)-pyrazolo[4,3-e]-1,2,4-triazolo[1,5-c]pyrimidine.

18. A method of treating hypertension, inflammation, allergic reactions, mast cell degranulation and cardiac hypoxia, and protecting against cerebral ischemia, comprising administering to a patient in need of treatment thereof an effective amount of a compound of claim 17.

19. A compound selected from the group of compounds consisting of:

5-[[(3-Chlorophenyl)amino]]carbonyl]amino-8-(2-isopentenyl)-2-(2-furyl)pyrazolo[4,3-e]1,2,4-triazolo[1,5-c]pyrimidine, and 5-[[(4-Methoxyphenyl)amino]carbonyl]amino-8-(2-isopentenyl)-2-(2-furyl)-pyrazolo[4,3-e]-1,2,4-triazolo[1,5-c]pyrimidine.

\* \* \* \* \*